United States Patent [19]

Bertram et al.

[11] Patent Number: 5,225,434
[45] Date of Patent: Jul. 6, 1993

[54] PESTICIDAL AND HERBICIDAL POLYCYCLIC 3-ARYL-PYRROLIDINE-2,4-DIONE DERIVATIVES

[75] Inventors: Heinz-Jürgen Bertram, Bonn; Reiner Fischer, Monheim; Hermann Hagemann, Leverkusen; Bernd-Wieland Krüger; Thomas Schenke, both of Bergisch Gladbach; Christoph Erdelen, Leichlingen; Birgit Krauskopf; Klaus Lürssen, both of Bergisch Gladbach; Hans-Joachim Santel, Leverkusen; Robert R. Schmidt, Bergisch-Gladbach; Ulrike Wachendorff-Neumann, Monheim, all of Fed. Rep. of Germany

[73] Assignee: Bayer Aktiengesellschaft, Leverkusen, Fed. Rep. of Germany

[21] Appl. No.: 651,679

[22] Filed: Feb. 6, 1991

[30] Foreign Application Priority Data

Feb. 13, 1990 [DE] Fed. Rep. of Germany ....... 4004321
Oct. 10, 1990 [DE] Fed. Rep. of Germany ....... 4032090

[51] Int. Cl.$^5$ ................. C07D 471/08; C07D 487/18; A01N 43/12; A01N 57/10
[52] U.S. Cl. ..................................... 514/411; 514/80; 514/294; 546/23; 546/94; 548/114; 548/428
[58] Field of Search ................ 548/428, 114; 514/411, 514/294, 80; 546/23, 94

[56] References Cited

FOREIGN PATENT DOCUMENTS 0262399 4/1988 European Pat. Off. .
0355599 8/1989 European Pat. Off. .

OTHER PUBLICATIONS

Liebigs Annalen der Chemie, No. 5, 1985, pp. 1095-1098, Wienheim, DE; R. Schmierer et al.: "Cyclisierung von N-Acylalanin- und N-Acylglycinestern".

Primary Examiner—Mary C. Lee
Assistant Examiner—Mary Susan H. Gabilan
Attorney, Agent, or Firm—Sprung Horn Kramer & Woods

[57] ABSTRACT

Insecticidal, acaricidal and herbicidal polycyclic 3-aryl-pyrrolidine-2,4-dione derivatives of the formula

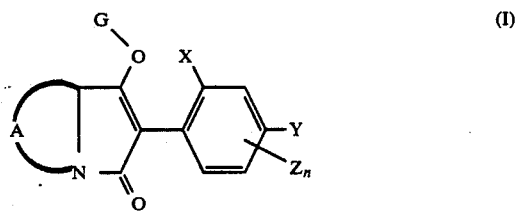

in which
A represents the radical of a bi-, tri- or polycyclic system which is optionally interrupted by further hetero atoms or groups of hetero atoms,
X represents alkyl, halogen or alkoxy,
Y represents hydrogen, alkyl, halogen, alkoxy or halogenoalkyl,
Z represents alkyl, halogen or alkoxy,
n represents a number from 0-3, and
G represents hydrogen or various organic radicals.

16 Claims, No Drawings

PESTICIDAL AND HERBICIDAL POLYCYCLIC 3-ARYL-PYRROLIDINE-2,4-DIONE DERIVATIVES

The invention relates to new polycyclic 3-arylpyrrolidine-2,4-dione derivatives, to a plurality of processes for their preparation, and to their use as insecticides, acaricides and herbicides.

Pharmaceutical properties have been described of 3-acyl-pyrrolidine-2,4-diones (S. Suzuki et al., Chem. Pharm. Bull. 15 1120 (1967)). N-phenyl-pyrrolidine-2,4-diones were furthermore synthesized by R. Schmierer and H. Mildenberger, Liebigs Ann. Chem. 1985 1095. A biological activity of these compounds has not been described.

EP-A 0,262,399 discloses compounds of a similar structure (3-aryl-pyrrolidin-2,4-diones), but no herbicidal, insecticidal or acaricidal action has been disclosed for these compounds.

New polycyclic 3-arylpyrrolidine-2,4-dione derivatives of the formula (I)

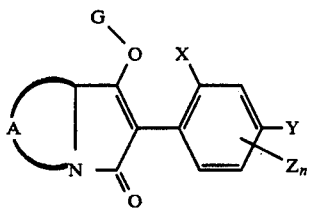

have now been found, in which
A represents the radical of a saturated or unsaturated bi-, tri- or polycyclic system which is optionally interrupted by further hetero atoms or groups of hetero atoms,
X represents alkyl, halogen or alkoxy,
Y represents hydrogen, alkyl, halogen, alkoxy or halogenoalkyl,
Z represents alkyl, halogen or alkoxy,
n represents a number from 0–3,
G represents hydrogen (a), or represents the groups

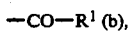
—CO—R$^1$ (b),

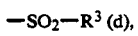
—SO$_2$—R$^3$ (d),

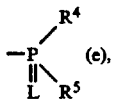

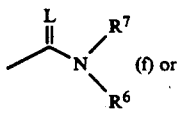

E (g), in which
E represents a metal ion equivalent or an ammonium ion,
L and M represents oxygen and/or sulphur,
R$^1$ represents optionally halogen-substituted alkyl, alkenyl, alkoxyalkyl, alkylthioalkyl, polyalkoxyalkyl or cycloalkyl which can be interrupted by hetero atoms, or represents optionally substituted phenyl, or represents optionally substituted phenylalkyl, substituted hetaryl, substituted phenoxyalkyl or substituted hetaryloxyalkyl, and
R$^2$ represents alkyl, alkenyl, alkoxyalkyl or polyalkoxyalkyl, each of which is optionally substituted by halogen, or represents optionally substituted phenyl or benzyl,
R$^3$, R$^4$ and R$^5$ independently of one another represent alkyl, alkoxy, alkylamino, dialkylamino, alkylthio, alkenylthio, alkinylthio or cycloalkylthio, each of which is optionally substituted by halogen, or represent optionally substituted phenyl, phenoxy or phenylthio, and
R$^6$ and R$^7$ independently of one another represent hydrogen, or represent alkyl, alkenyl, alkoxy or alkoxyalkyl, each of which is optionally substituted by halogen, or represent optionally substituted phenyl, or represent optionally substituted benzyl, or where R$^6$ and R$^7$ together represent an alkylene radical which is optionally interrupted by oxygen.

Taking into account the various meanings (a), (b), (c), (d), (e), (f) and (g) of the group G of the general formula (I), the following main structures (Ia) to (Ig) result:

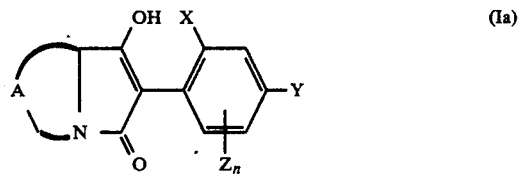
(Ia)

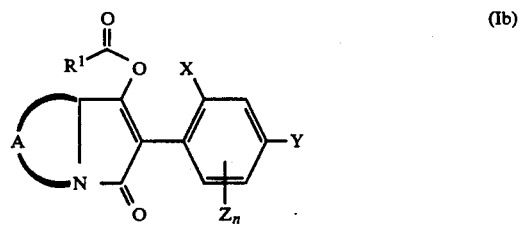
(Ib)

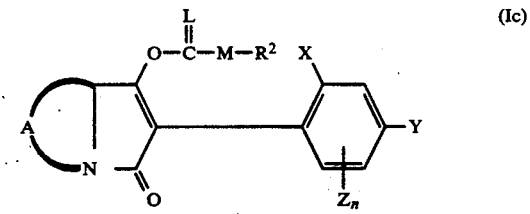
(Ic)

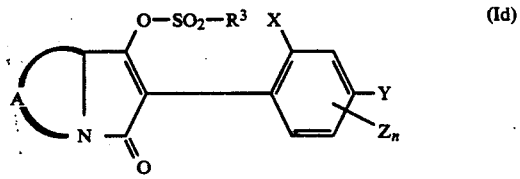
(Id)

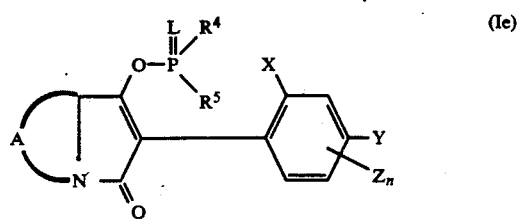
(Ie)

-continued (If)

(Ig)

wherein A, E, L, M, X, Y, $Z_n$, $R^1$, $R^2$, $R^3$, $R^4$, $R^5$, $R^6$ and $R^7$ have the abovementioned meanings.

Because of one or more centers of chirality, the compounds of the formula (Ia)–(If) are generally obtained as a mixture of stereoisomers. They can be used in the form of their mixtures of diastereomers and also as pure diastereomers or enantiomers.

Furthermore, it has been found that 3-arylpyrrolidone-2,4-diones or their enols of the formula (Ia)

(Ia)

in which A, X, Y, Z and n have the abovementioned meanings, are obtained when (A) N-acylamino acid esters of the formula (II)

(II)

in which

A, X, Y, Z and n have the abovementioned meanings and $R^8$ represents alkyl, are subjected to intramolecular condensation in the presence of a diluent and in the presence of a base.

(B) Furthermore, it has been found that compounds of the formula (Ib)

(Ib)

in which A, X, Y, Z, $R^1$ and n have the abovementioned meanings, are obtained when compounds of the formula (Ia)

(Ia)

in which A, X, Y, Z and n have the abovementioned meanings, are reacted

α) with acid halides of the general formula (III)

$$Hal-C(=O)-R^1 \quad (III)$$

in which $R^1$ has the abovementioned meaning and

Hal represents halogen, in particular chlorine and bromine, if appropriate in the presence of a diluent and if appropriate in the presence of an acid-binding agent, or β) with carboxylic anhydrides of the general formula (IV)

$$R^1-CO-O-CO-R^1 \quad (IV)$$

in which $R^1$ has the abovementioned meaning, if appropriate in the presence of a diluent and if appropriate in the presence of an acid-binding agent.

(C) Furthermore, it has been found that compounds of the formula (Ic)

(Ic)

in which

A, X, Y, Z, $R^2$ and n have the abovementioned meanings,

L represents oxygen and

M represents oxygen or sulphur, are obtained when compounds of the formula (Ia)

(Ia)

in which A, X, Y, Z and n have the abovementioned meanings, are reacted with chloroformic ester or chloroformic thioester of the general formula (V)

$$R^2-M-CO-Cl \quad (V)$$

in which $R^2$ and M have the abovementioned meanings, if appropriate in the presence of a diluent and if appropriate in the presence of an acid-binding agent.

(D) Furthermore, it has been found that compounds of the formula (Ic)

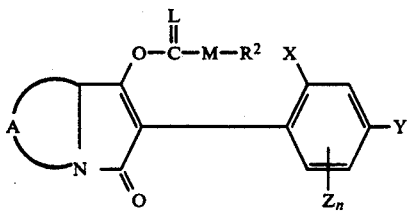
(Ic)

in which
A, $R^2$, X, Y, Z and n have the abovementioned meanings,
L represents sulphur and
M represents oxygen or sulphur, are obtained when compounds of the formula (Ia)

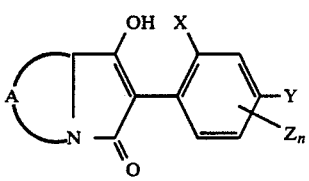
(Ia)

in which A, X, Y, Z and n have the abovementioned meanings, are reacted
α) with chloromonothioformic esters or chlorodithioformic esters of the general formula (VI)

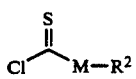
(VI)

in which M and $R^2$ have the abovementioned meanings, if appropriate in the presence of a diluent and if appropriate in the presence of an acid-binding agent, or
β) with carbon disulphide and then with alkyl halides of the general formula (VII)

 (VII)

in which
$R^2$ has the abovementioned meaning and
Hal represents chlorine, bromine or iodine.

(E) Furthermore, it has been found that compounds of the formula (Id)

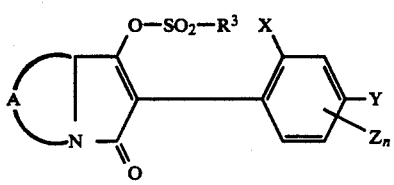
(Id)

in which A, X, Y, Z, $R^3$ and n have the abovementioned meanings, are obtained when compounds of the formula (Ia)

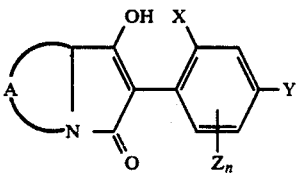
(Ia)

in which A, X, Y, Z and n have the abovementioned meanings, are reacted with sulphonyl chlorides of the general formula (VIII)

(VIII)

in which $R^3$ has the abovementioned meaning, if appropriate in the presence of a diluent and if appropriate in the presence of an acid-binding agent.

(F) Furthermore, it has been found that 3-aryl-pyrrolidine-2,4-diones of the formula (Ie)

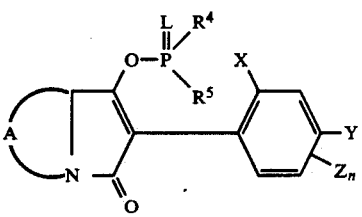
(Ie)

in which A, L, X, Y, Z, $R^4$, $R^5$ and n have the abovementioned meanings, are obtained when 3-aryl-pyrrolidine-2,4-diones or their enols of the formula (Ia)

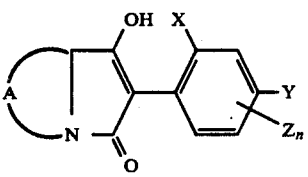
(Ia)

in which A, X, Y, Z and n have the abovementioned meanings, are reacted with phosphorus compounds of the general formula (IX)

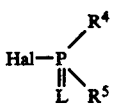
(IX)

in which
L, $R^4$ and $R^5$ have the abovementioned meanings, and
Hal represents halogen, in particular chlorine and bromine,
if appropriate in the presence of a diluent and if appropriate in the presence of an acid-binding agent.

(G) Furthermore, it has been found that compounds of the formula (If)

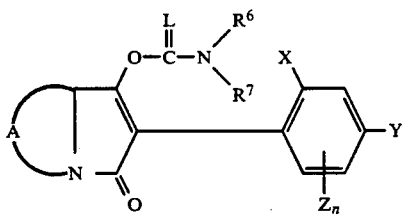

in which A, L, X, Y, Z, R⁶, R⁷ and n have the abovementioned meanings, are obtained when compounds of the formula (Ia)

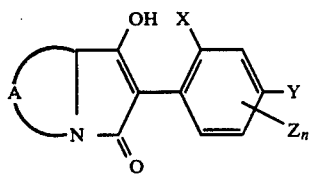

in which A, X, Y, Z and n have the abovementioned meanings, are reacted

α) with isocyanates of the general formula (X)

$$R^6-N=C=O \quad (X)$$

in which R⁶ has the abovementioned meaning, if appropriate in the presence of a diluent and if appropriate in the presence of a catalyst, or β) with carbamoyl chlorides or thiocarbamoyl chlorides of the general formula (XI)

in which L, R⁶ and R⁷ have the abovementioned meanings, if appropriate in the presence of a diluent and if appropriate in the presence of an acid-binding agent.

(H) Furthermore, it has been found that compounds of the formula (Ig)

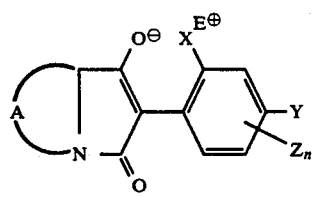

in which X, Y, Z, A and n have the abovementioned meanings and E represents a metal ion equivalent or an ammonium ion, are obtained when compounds of the formula (Ia)

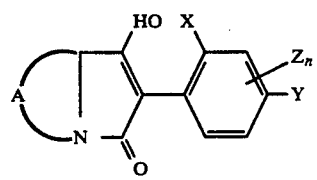

in which X, Y, Z, A and n have the abovementioned meanings, are reacted with metal hydroxides or amines of the general formulae (XII) and (XIII)

$$Me_sOH_t \quad (XII)$$

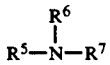

in which

Me represents mono- or divalent metal ions, s and t represent the number 1 or 2 and R⁵, R⁶ and R⁷ independently of one another represent hydrogen and alkyl, if appropriate in the presence of a diluent.

Furthermore, it has been found that the new polycyclic 3-arylpyrrolidine-2,4-dione derivatives are distinguished by outstanding insecticidal, acaricidal and herbicidal actions.

Preferred polycyclic 3-arylpyrrolidine-2,4-dione derivatives of the formula (I) are those in which A represents the radical of a saturated or unsaturated bi-, tri- or polycyclic system which is optionally interrupted by further hetero atoms or groups of hetero atoms, X represents $C_1$–$C_6$-alkyl, halogen or $C_1$–$C_6$-alkoxy, Y represents hydrogen, $C_1$–$C_6$-alkyl, halogen, $C_1$–$C_6$-alkoxy or $C_1$–$C_3$-halogenoalkyl, Z represents $C_1$–$C_6$-alkyl, halogen or $C_1$–$C_6$-alkoxy, n represents a number from 0 to 3, G represents hydrogen (a) or represents the groups

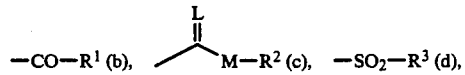

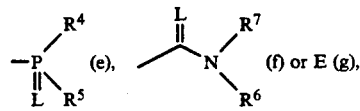

in which

E represents a metal ion equivalent or an ammonium ion,

L and M represents oxygen and/or sulphur,

R¹ represents optionally halogen-substituted: $C_1$–$C_{20}$-alkyl, $C_2$–$C_{20}$-alkenyl, $C_1$–$C_8$-alkoxy-$C_2$–$C_8$-alkyl, $C_1$–$C_8$-alkylthio-$C_2$–$C_8$-alkyl, $C_1$–$C_8$-polyalkoxyl-$C_2$–$C_8$-alkyl or cycloalkyl which has 3–8 ring atoms and which can be interrupted by oxygen and/or sulphur atoms, or phenyl optionally substituted by halogen, nitro, $C_1$–$C_6$-alkyl, $C_1$–$C_6$-alkoxy, $C_1$–$C_6$-halogenoalkyl or $C_1$–$C_6$-halogenoalkoxy; or represents phenyl-$C_1$–$C_6$-alkyl optionally substituted by halogen, $C_1$–$C_5$-alkyl, $C_1$–$C_6$-alkoxy, $C_1$–$C_6$-halogenoalkyl or $C_1$–$C_6$-halogenoalkoxy; or represents hetaryl which is optionally substituted by halogen and/or $C_1$–$C_6$-alkyl, or represents phenoxy-$C_1$–$C_6$-alkyl optionally substituted by halogen or $C_1$–$C_6$-alkyl, or represents hetaryloxy-$C_1$–$C_6$-alkyl optionally substituted by halogen, amino or $C_1$–$C_6$-alkyl, R² represents $C_1$–$C_{20}$-alkyl, $C_2$–$C_{20}$-alkenyl, $C_1$–$C_8$-alkoxy-$C_2$–$C_8$-alkyl or $C_1$–$C_8$-polyalkoxy-$C_2$–$C_8$-alkyl, each of which is optionally substituted by halogen, or represents phenyl or benzyl optionally substituted by halogen, nitro, $C_1-C_6$-alkyl, $C_1-C_6$-alkoxy or $C_1-C_6$-halogenoalkyl, $R^3$, $R^4$ and $R^5$ independently of one another represent $C_1-C_8$-alkyl, $C_1-C_8$-alkoxy, $C_1-C_8$-alkylamino, di-($C_1-C_8$)-alkylamino, $C_1-C_8$-alkylthio, $C_2-C_5$-alkenylthio, $C_2-C_5$-alkinylthio or $C_3-C_7$-cycloalkylthio, each of which is optionally substituted by halogen, or represent phenyl, phenoxy or phenylthio, each of which is optionally substituted by halogen, nitro, cyano, $C_1-C_4$-alkoxy, $C_1-C_4$-halogenoalkoxy, $C_1-C_4$-alkylthio, $C_1-C_4$-halogenoalkylthio, $C_1-C_4$-alkyl or $C_1-C_4$-halogenoalkyl, and $R^6$ and $R^7$ independently of one another represent $C_1-C_{20}$-alkyl, $C_1-C_{20}$-alkoxy, $C_2-C_8$-alkenyl or $C_1-C_{20}$-alkoxy-$C_1-C_{20}$-alkyl, each of which is optionally substituted by halogen, or represent phenyl which is optionally substituted by halogen, $C_1-C_{20}$-halogenoalkyl, $C_1-C_{20}$-alkyl or $C_1-C_{20}$-alkoxy, or represent benzyl which is optionally substituted by halogen, $C_1-C_{20}$-alkyl, $C_1-C_{20}$-halogenoalkyl or $C_1-C_{20}$-alkoxy, or together represent a $C_2-C_6$-alkylene chain which is optionally interrupted by oxygen.

Because of one or more centers of chirality, the compounds of the formula (Ia)–(If) are generally obtained as mixtures of stereoisomers. They can be used in the form of their mixtures of diastereomers as well as pure diastereomers or enantiomers.

Particularly preferred compounds of the formula (I) are those in which the group

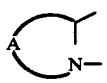

has one of the following meanings 1 to 29:

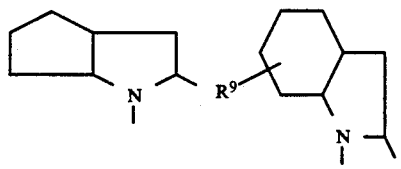

1     2

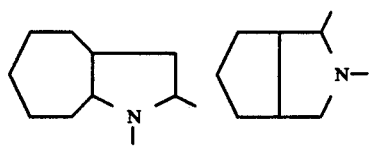

3     4

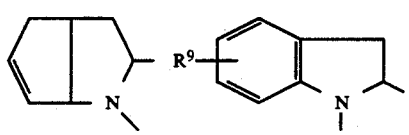

5     6

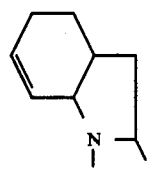 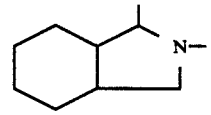

7     8

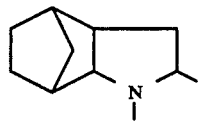 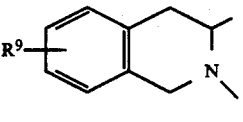

9     10

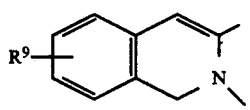 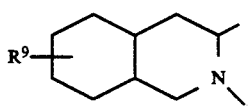

11     12

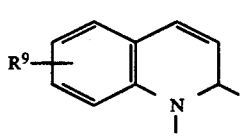 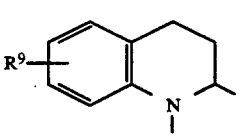

13     14

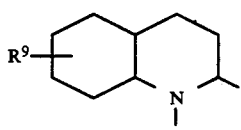 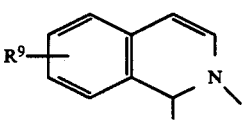

15     16

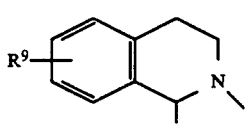 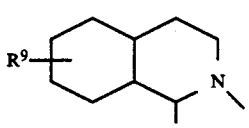

17     18

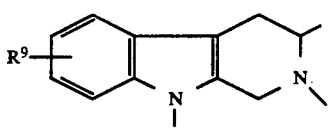

19

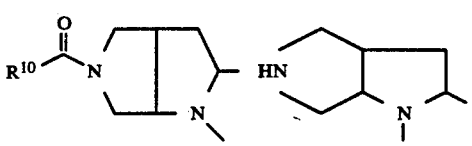

20     21

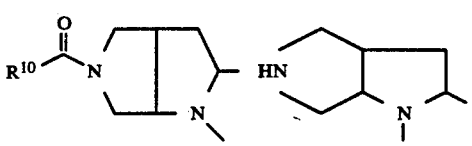

22     23

-continued

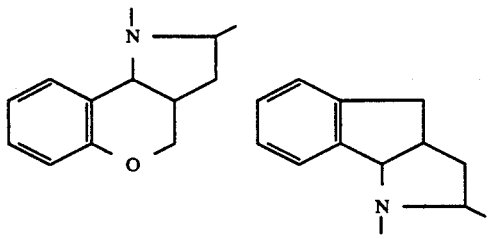

24     25

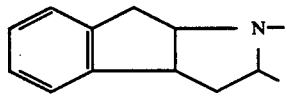

26

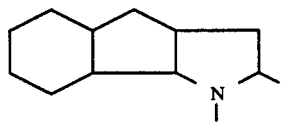

27

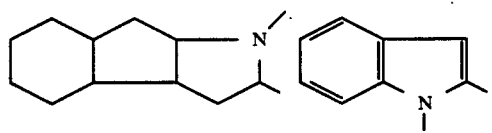

28     29

X represents $C_1$-$C_4$-alkyl, halogen or $C_1$-$C_4$-alkoxy,
Y represents hydrogen, $C_1$-$C_4$-alkyl, halogen, $C_1$-$C_4$-alkoxy or $C_1$-$C_2$-halogenoalkyl,
Z represents $C_1$-$C_4$-alkyl, halogen or $C_1$-$C_4$-alkoxy,
n represents a number from 0-3,
G represents hydrogen (a), or represents the groups $-CO-R^1$ (b),   $M-R^2$ (c),   $-SO_2-R^3$ (d), $$-\overset{R^4}{\underset{\underset{L}{\|}}{P}}\diagdown_{R^5} \text{ (e),} \quad \diagup\overset{\underset{\|}{L}}{\underset{R^6}{\diagdown}}N\diagup^{R^7} \text{ (f) or E (g),}$$

in which
E represents a metal ion equivalent or an ammonium ion,
L and M in each case represents oxygen and/or sulphur,
$R^1$ represents optionally halogen-substituted $C_1$-$C_{16}$-alkyl, $C_2$-$C_{16}$-alkenyl, $C_1$-$C_6$-alkoxy-$C_2$-$C_6$-alkyl, $C_1$-$C_{16}$-alkylthio-$C_2$-$C_6$-alkyl, $C_1$-$C_6$-polyalkoxy-$C_2$-$C_6$-alkyl and cycloalkyl which has 3-7 ring atoms and which can be interrupted by 1-2 oxygen and/or sulphur atoms, or represents phenyl optionally substituted by Halogen, nitro, $C_1$-$C_4$-alkyl, $C_1$-$C_4$-alkoxy, $C_1$-$C_3$-halogenoalkyl or $C_1$-$C_3$-halogenoalkoxy, or represents phenyl-$C_1$-$C_4$-alkyl optionally substituted by halogen, $C_1$-$C_4$-alkyl, $C_1$-$C_4$-alkoxy, $C_1$-$C_3$-halogenoalkyl or $C_1$-$C_3$-halogenoalkoxy, or represents hetaryl optionally substituted by halogen or $C_1$-$C_6$-alkyl, or represents phenoxy-$C_1$-$C_5$-alkyl optionally substituted by halogen or $C_1$-$C_4$-alkyl, or represents hetaryloxy-$C_1$-$C_5$-alkyl which is optionally substituted by halogen, amino or $C_1$-$C_4$-alkyl, $R^2$ represents optionally halogen-substituted $C_1$-$C_{16}$-alkyl, $C_2$-$C_{16}$-alkenyl, $C_1$-$C_{16}$-alkox-$C_2$-$C_6$-alkyl or $C_1$-$C_6$-polyalkoxy-$C_2$-$C_6$-alkyl, or represents phenyl or benzyl optionally substituted by halogen, nitro, $C_1$-$C_4$-alkyl, $C_1$-$C_3$-alkoxy or $C_1$-$C_3$-halogenoalkyl, $R^3$, $R^4$ and $R^5$ independently of one another represent $C_1$-$C_6$-alkyl, $C_1$-$C_6$-alkoxy, $C_1$-$C_6$-alkylamino, di-($C_1$-$C_6$)-alkylamino, $C_1$-$C_6$-alkylthio, $C_3$-$C_4$-alkenylthio, $C_2$-$C_4$-alkinylthio or $C_3$-$C_6$-cycloalkylthio, each of which is optionally substituted by halogen, or represents phenyl, phenoxy or phenylthio, each of which is optionally substituted by fluorine, chlorine, bromine, nitro, cyano, $C_1$-$C_3$-alkoxy, $C_1$-$C_3$-halogenoalkoxy, $C_1$-$C_3$-alkylthio, $C_1$-$C_3$-halogenoalkylthio, $C_1$-$C_3$-alkyl or $C_1$-$C_3$-halogenoalkyl, $R^6$ and $R^7$ independently of one another represents $C_1$-$C_{20}$-alkyl, $C_1$-$C_{20}$-alkoxy, $C_2$-$C_8$-alkenyl or $C_1$-$C_{20}$-alkoxy-$C_1$-$C_{20}$-alkyl, each of which is optionally substituted by halogen, or represents phenyl which is optionally substituted by halogen, $C_1$-$C_5$-halogenoalkyl, $C_1$-$C_5$-alkyl or $C_1$-$C_5$-alkoxy, or represents benzyl which is optionally substituted by halogen, $C_1$-$C_5$-alkyl, $C_1$-$C_5$-halogenoalkyl or $C_1$-$C_5$-alkoxy, $R^9$ represents hydrogen, halogen, or represents $C_1$-$C_2$-alkyl or $C_1$-$C_2$-alkoxy, each of which is optionally substituted by halogen, and $R^{10}$ represents $C_1$-$C_7$-alkoxy, amino, $C_1$-$C_4$-alkylamino or $C_1$-$C_4$-dialkylamino.

Very particularly preferred compounds of the formula (I) are those in which the group

has one of the following meanings 1 to 29:

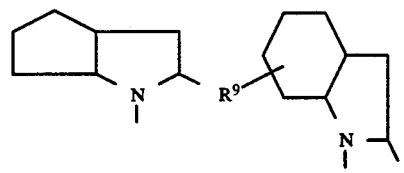

1     2

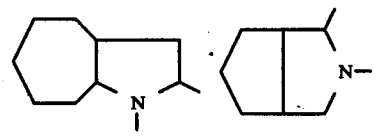

3     4

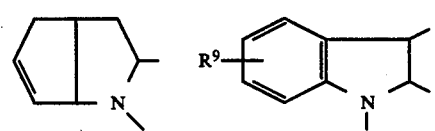

5     6

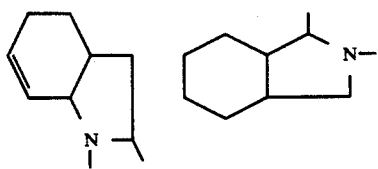
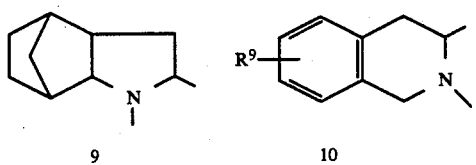
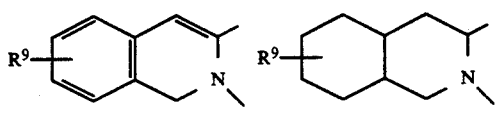
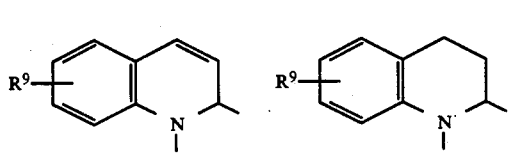
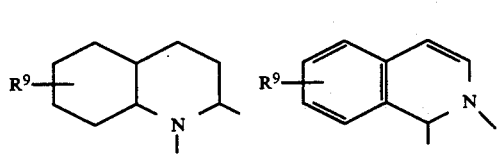
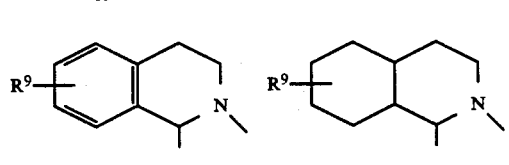
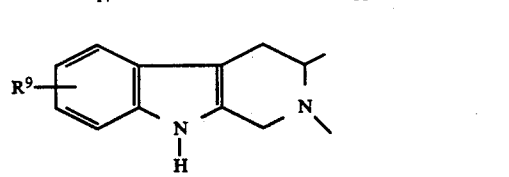
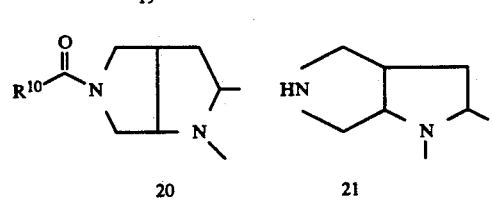

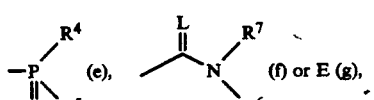

X represents methyl, ethyl, propyl, i-propyl, fluorine, chlorine, bromine, methoxy or ethoxy, Y represents hydrogen, methyl, ethyl, propyl, i-propyl, butyl, i-butyl, tert.-butyl, fluorine, chlorine, bromine, methoxy, ethoxy or trifluoromethyl, Z represents methyl, ethyl, i-propyl, butyl, i-butyl, tert.-butyl, fluorine, chlorine, bromine, methoxy or ethoxy, n represents a number from 0–3, G represents hydrogen (a), or represents the groups

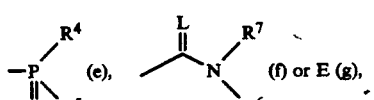

in which

E represents a metal ion equivalent or an ammonium ion,

L and M represents oxygen and/or sulphur, $R^1$ represents optionally fluorine- or chlorine-substituted $C_1$–$C_{14}$-alkyl, $C_2$–$C_{14}$-alkenyl, $C_1$–$C_4$-alkoxy-$C_2$–$C_6$-alkyl, $C_1$–$C_4$-alkylthio-$C_2$–$C_6$-alkyl, $C_1$–$C_4$- polyalkoxy-$C_2$-$C_4$-alkyl or cycloalkyl which has 3–6 ring atoms and which can be interrupted by 1–2 oxygen and/or sulphur atoms, or represents phenyl optionally substituted by fluorine, chlorine, bromine, methyl, ethyl, propyl, i-propyl, methoxy, ethoxy, trifluoromethyl, trifluoromethoxy or nitro, or represents phenyl-$C_1$-$C_3$-alkyl, optionally substituted by fluorine, chlorine, bromine, methyl, ethyl, propyl, i-propyl, methoxy, ethoxy, trifluoromethyl or trifluoromethoxy, or represents pyridyl, pyrimidyl, thiazolyl or pyrazolyl optionally substituted by fluorine, chlorine, bromine, methyl or ethyl, or represents optionally by fluorine, chlorine, methyl, ethyl-substituted phenoxy-$C_1$-$C_4$-alkyl, or represents pyridyloxy-$C_1$-$C_4$-alkyl, pyrimidyloxy-$C_1$-$C_4$-alkyl or thiazolyloxy-$C_1$-$C_4$-alkyl optionally substituted by fluorine, chlorine, amino, methyl or ethyl.

$R^2$ represents $C_1$-$C_{14}$-alkyl, $C_2$-$C_{14}$-alkenyl, $C_1$-$C_4$-alkoxy-$C_2$-$C_6$-alkyl or $C_1$-$C_4$-polyalkoxy-$C_2$-$C_6$-alkyl, each of which is optionally substituted by fluorine or chlorine, or represents phenyl or benzyl, each of which is optionally substituted by fluorine, chlorine, nitro, methyl, ethyl, propyl, i-propyl, methoxy, ethoxy or trifluoromethyl, $R^3$, $R^4$ and $R^5$ independently of one another represent $C_1$-$C_4$-alkyl, $C_1$-$C_4$-alkoxy, $C_1$-$C_4$-alkylamino, di-($C_1$-$C_4$-alkyl)-amino or $C_1$-$C_4$-alkylthio, each of which is optionally substituted by fluorine or chlorine, or represent phenyl, phenoxy or phenylthio, each of which is optionally substituted by fluorine, chlorine, bromine, nitro, cyano, $C_1$-$C_2$-alkoxy, $C_1$-$C_4$-fluoroalkoxy, $C_1$-$C_2$-chloroalkoxy, $C_1$-$C_2$-alkylthio, $C_1$-$C_2$-fluoroalkylthio, $C_1$-$C_2$-chloroalkylthio or $C_1$-$C_3$-alkyl, $R^6$ and $R^7$ independently of one another represents $C_1$-$C_{10}$-alkyl, $C_1$-$C_{10}$-alkoxy or $C_1$-$C_{10}$-alkoxy-($C_1$-$C_{10}$)alkyl, each of which is optionally substituted by fluorine, chlorine or bromine, or represents phenyl which is optionally substituted by fluorine, chlorine, bromine, $C_1$-$C_{20}$-halogenoalkyl, $C_1$-$C_{20}$-alkyl or $C_1$-$C_4$-alkoxy, or represents benzyl which is optionally substituted by fluorine, chlorine, bromine, $C_1$-$C_4$-alkyl, $C_1$-$C_4$-halogenoalkyl or $C_1$-$C_4$-alkoxy, $R^9$ represents hydrogen or halogen, or represents $C_1$-$C_2$-alkyl or $C_1$-$C_2$-alkoxy, each of which is optionally substituted by halogen, and $R^{10}$ represents methoxy, ethoxy, propoxy, iso-propoxy, butoxy, iso-butoxy, sec.-butoxy, tert.-butoxy, phenoxy, benzyloxy, amino, $C_1$-$C_2$-alkylamino or $C_1$-$C_2$-dialkylamino.

If, according to process (A), ethyl N-2,6-dichlorophenyl-acetyl-perhydroquinoline-2-carboxylate is used, the course of the process according to the invention can be represented by the following equation:

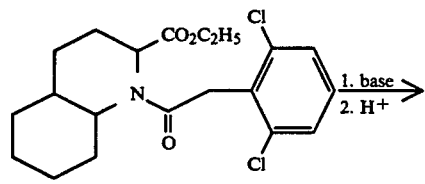

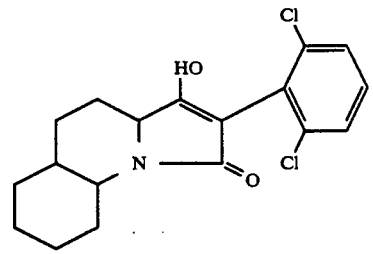

If, according to process (B) (variant α), 10-(2,4,6-trimethylphenyl)-1-aza-tricyclo(6,3,0$^{1.8}$,0$^{2.6}$)-undecane-9,11-dione and pivaloyl chloride are used as starting substances, the course of the process according to the invention can be represented by the following equation:

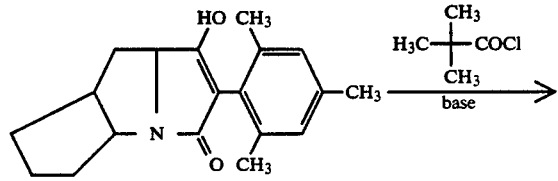

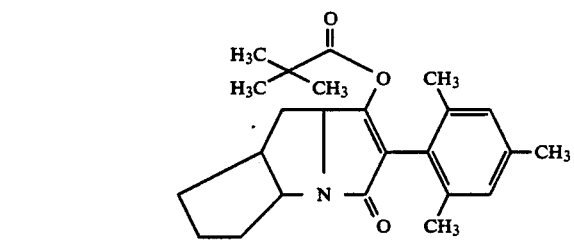

If, according to process (B) (variant β), 12-(2,4,5-trimethylphenyl)-1-aza-tricyclo-(8,3,0$^{1.10}$,0$^{3.8}$)-tridecane-11,13-dione and acetic anhydride are used as starting compounds, the course of the process according to the invention can be represented by the following equation:

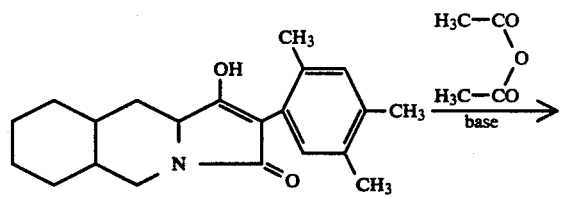

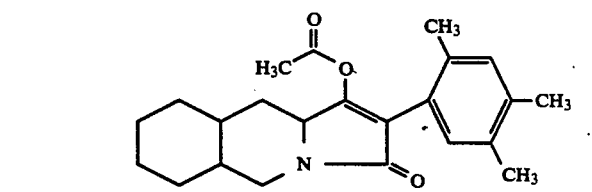

If, according to process (C), 12-(2,4-dichlorophenyl)-1-aza-tricyclo-(8,3,0$^{1.10}$,0$^{2.7}$)-tridecane-11,13-dione and ethoxyethyl chloroformate are used as starting compounds, the course of the process according to the invention can be represented by the following equation:

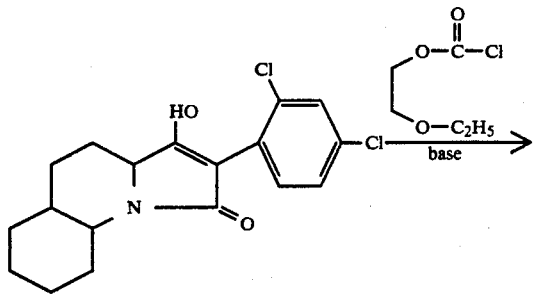

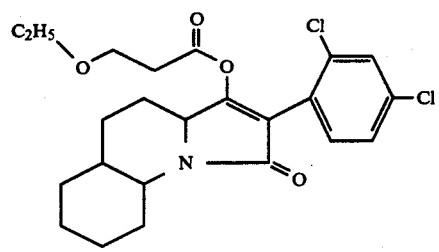

If, according to process (D$_\alpha$), 11-(2,4,6-trimethylphenyl)-1-aza-tricyclo-(7,3,0$^{1.9}$,0$^{3.8}$) -dodecane-10,12-dione and methyl chloromonothioformate are used as starting materials, the course of the reaction can be represented as follows:

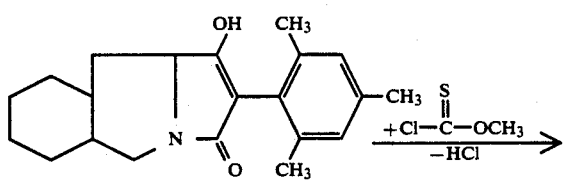

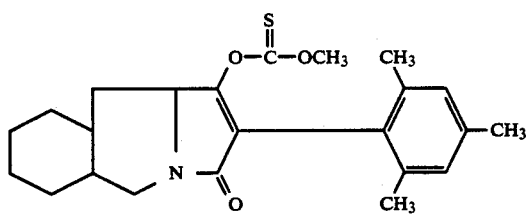

If, according to process (D$_\beta$), 11-(2,4,6-trimethylphenyl)1-aza-tricyclo-(7,3,0$^{1.8}$,0$^{2.7}$) -dodecane-10,12-dione, carbon disulphide and methyl iodide are used as starting components, the course of the reaction can be represented as follows:

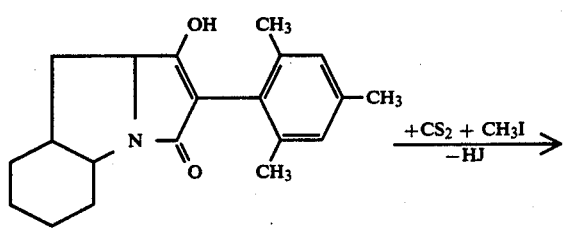

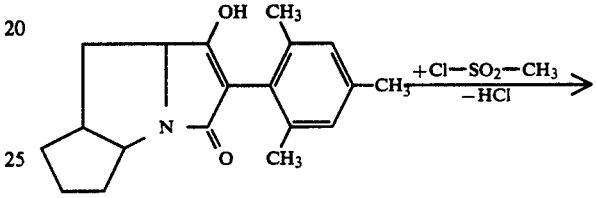

If, according to process (E), 10-(2,4,6-trimethylphenyl)-1-aza-tricyclo-(6,3,0$^{1.8}$,0$^{2.6}$)-undecane-9,11-dione and methanesulphonyl chloride are used as starting materials, the course of the reaction can be represented by the following equation:

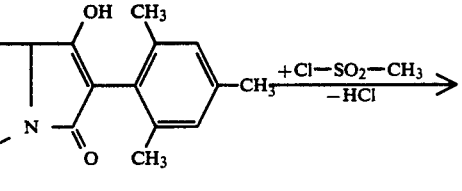

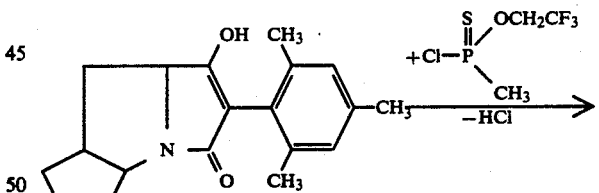

If, according to process (F), 10-(2,4,6-trimethylphenyl)-1,4-diaza-(4-N-ethoxycarbonyl)-tricyclo-(6,3,0$^{1.8}$,0,$^{2.6}$)-undecane-9,11-dione and 2,2,2-trifluoroethyl methane-thiochlorophosphonate are used as starting materials, the course of the reaction can be represented by the following equation:

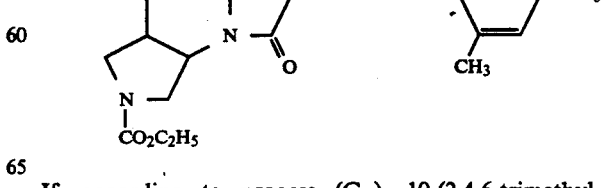

If, according to process (G$_\alpha$), 10-(2,4,6-trimethyl-phenyl)-1-aza-tricyclo-(6,3,0$^{1.8}$,0$^{2.6}$)-undecane-9,11-dione and ethyl isocyanate are used as starting materials, the course of the reaction can be represented by the following equation:

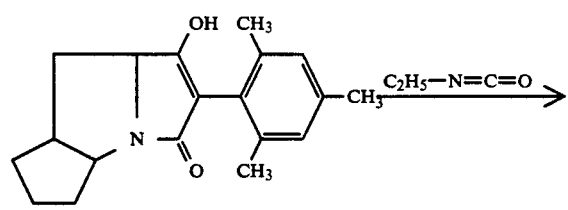

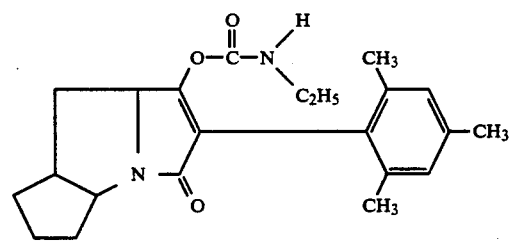

If, according to process (Gβ),11-(2,4,6-trimethylphenyl)-1-aza-tricyclo-(7,3,0^{1.9},0^{2.7})-dodecane-10,12-dione and dimethylcarbamoyl chloride are used as starting materials, the course of the reaction can be represented by the following equation:

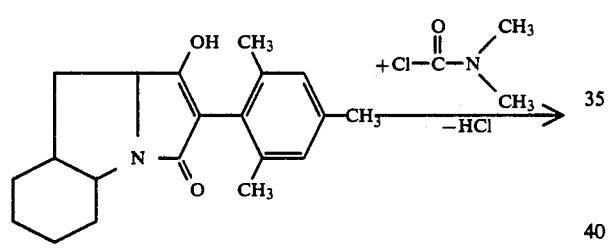

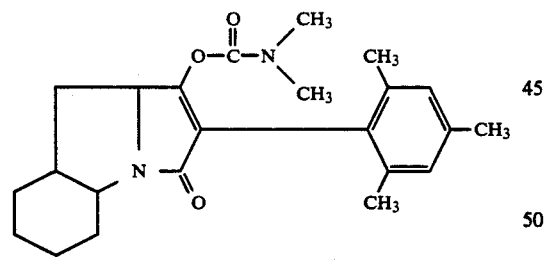

If, according to process (H), 10-(2,4,6-trimethylphenyl)-1-aza-tricyclo-(6,3,0^{1.8},0^{2.6})-undecane-9,11-dione and NaOH are used as components, the course of the process according to the invention can be represented by the following equation:

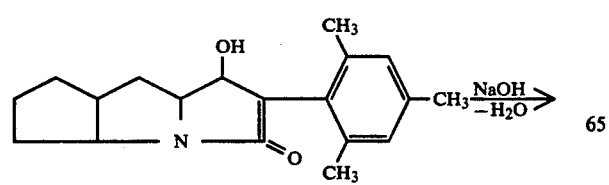

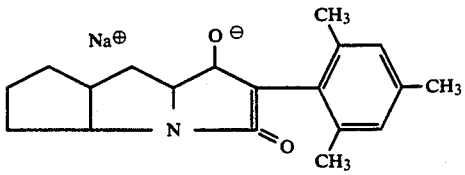

The compounds of the formula (II)

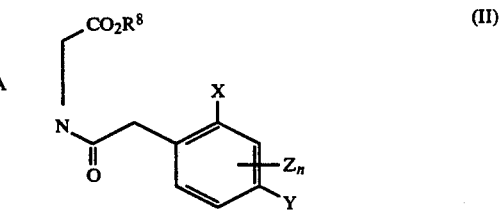

in which A, X, Y, Z, n and $R^8$ have the abovementioned meanings, and which are required as starting substances in the above process (A) are known or may be prepared in a simple manner by methods known in principle. For example, acylamino acid esters of the formula (II) are obtained when a) amino acid esters of the formula (XIV)

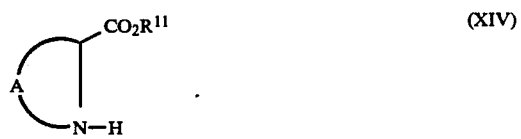

in which
$R^{11}$ represents hydrogen (XIVa) or alkyl (XIVb) and
A has the abovementioned meaning, are acyclated with phenylacetic halides of the formula (XV)

in which
X, Y, Z and n have the abovementioned meanings and
Hal represents chlorine or bromine (Chem. Reviews 52 237–416 (1953));
or when acylamino acids of the formula (IIa)

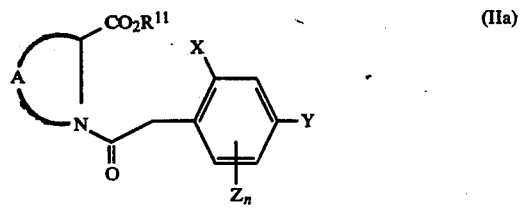

in which
A, X, Y, Z and n have the abovementioned meanings and $R^{11}$ represents hydrogen, are esterified (Chem. Ind. (London) 1568 (1968).

For example, compounds of the formula (IIa) are obtainable from the phenylacetic halides of the formula (XV) and amino acids of the formula (XIV a) by the method of Schotten-Baumann (Organikum [Laboratory Practical of Organic Chemistry], 9th edition 446 (1970) VEB Deutscher Verlag der Wissenschaften, Berlin).

The following compounds of the formula (II) may be mentioned by way of example:
1. ethyl 2-aza-bicyclo-(3,3,0)-octane-N-(2,4-dichlorophenyl-acetyl)-3-carboxylate
2. ethyl 2-aza-bicyclo-(3,3,0)-octane-N-(2,6-dichlorophenylacetyl)-3-carboxylate
3. ethyl 2-aza-bicyclo-(3,3,0)-octane-N-(2,4,6-trichlorophenylacetyl-3-carboxylate
4. ethyl 2-aza-bicyclo-(3,3,0)-octane-N-(2,4-dimethylphenylacetyl)-3-carboxylate
5. ethyl 2-aza-bicyclo-(3,3,0)-octane-N-(2,6-dimethylphenylacetyl)-3-carboxylate
6. ethyl 2-aza-bicyclo-(3,3,0)-octane-N-(2,4,6-trimethylphenylacetyl)-3-carboxylate
7. ethyl 7-aza-bicyclo-(4,3,0)-nonane-N-(2,4,6-trimethylphenylacetyl)-8-carboxylate
8. ethyl 8-aza-bicyclo-(5,3,0)-decane-N-(2,4,6-trimethylphenylacetyl)-9-carboxylate
9. ethyl 3-aza-bicyclo-(3,3,0)-octane-N-(2,4,6-trimethylphenylacetyl)-2-carboxylate
10. ethyl 3-aza-bicyclo(3,3,0)-oct-7-ene-N-(2,4,6-trimethylphenylacetyl)-3-carboxylate
11. ethyl inodolin-N-(2,4,6-trimethylphenyl-acetyl-(2-carboxylate
12. ethyl 9-aza-bicyclo-(4,3,0)-non-2-ene-N-(2,4,6-trimethylphenyl-acetyl)-8-carboxylate
13. ethyl 8-aza-bicyclo-(4,3,0)-nonane-N-(2,4,6-trimethylphenyl-acetyl)-7-carboxylate
14. ethyl 7-aza-tricyclo-(4,3,1$^{2.5}$,0$^{1.6}$)-decane-N-(2,4,6-trimethylphenyl-acetyl)-8-carboxylate
15. ethyl 1,2-dihydroquinoline-N-(2,4,6-trimethylphenylacetyl)-2-carboxylate
16. ethyl 1,2,3,4-tetrahydroquinoline-N-(2,4,6-trimethylphenylacetyl)-2-carboxylate
17. ethyl perhydroquinoline-N-(2,4,6-trimethylphenylacetyl)-2-carboxylate
18. ethyl 1,2-dihydroisoquinoline-N-(2,4,6-trimethylphenylacetyl)-2-carboxylate
19. ethyl 1,2,7,8-tetrahydroisoquinoline-N-(2,4,6-trimethylphenylacetyl)-2-carboxylate
20. ethyl perhydroisoquinoline-N-(2,4,6-trimethylphenylacetyl)-2-carboxylate
21. ethyl perhydroindole-N-(2,4,6-trimethylphenylacetyl)-2-carboxylate
22. ethyl 2,7-diaza-7-(ethoxycarbonyl)-bicyclo-(3.3.0)-octane-N-(2,4,6-trimethylphenylacetyl)-3-carboxylate
23. ethyl 10-aza-tricyclo-(7,3,0$^{1.9}$,0$^{3.8}$)-dodecane-(2,4,6-trimethylphenylacetyl)-11-carboxylate
24. ethyl 10-aza-tricyclo-(7,3,0$^{1.9}$,0$^{2.7}$)-dodecane-(2,4,6-trimethylphenylacetyl)-11-carboxylate.

Compounds of the formula XIV in which A, B and $R^{11}$ have the abovementioned meanings, are known or can be obtained by processes known from the literature (Henning, R., Urbach, H., Tetrahedron Lett. 24, 5339–5342 (1983); EP-A-52,870; US-A-4,291,163; EP-A-173,199; Urbach, H, Henning, R. Tetrahedron Lett. 26, 1839–1842 (1985).

Process (A) is characterized in that compounds of the formula (II) in which A, X, Y, Z, n and $R^8$ have the abovementioned meanings are subjected to intramolecular condensation in the presence of bases.

Diluents which can be employed in process (A) according to the invention are all inert organic solvents. The following can preferably be used: hydrocarbons, such as toluene and xylene, furthermore ethers, such as dibutyl ether, tetrahydrofuran, dioxane, glycol dimethyl ether and diglycol dimethyl ether, and furthermore polar solvents, such as dimethyl sulphoxide, sulpholane, dimethylformamide and N-methyl-pyrrolidone.

Bases (deprotonating agents) which can be employed when carrying out process (A) according to the invention are all customary proton acceptors. The following can preferably be used: alkali metal oxides, alkai metal hydroxides, alkali metal carbonates, alkaline earth metal oxides, alkaline earth metal hydroxides and alkaline earth metal carbonates, such as sodium hydroxide, potassium hydroxide, magnesium oxide, calcium oxide, sodium carbonate, potassium carbonate and calcium carbonate, it also being possible for these compounds to be employed in the presence of phase-transfer catalysts such as, for example, triethylbenzylammonium chloride, te tr abutylammonium bromide, Adogen 464 (methyltrialkyl ($C_8$-$C_{10}$)ammonium chloride) or TDA (tris-(methoxyethoxyethyl)-amine). Furthermore alkali metals like sodium or potassium can be used.

The following can furthermore be employed: alkali metal amides, alkali metal hydrides, alkaline earth metal amides and alkaline earth metal hydrides such as sodium amide, sodium hydride and calcium hydride, and moreover also alkali metal alcoholates such as sodium methylate, sodium ethylate and potassium tert.-butylate.

When carrying out process (A) according to the invention, the reaction temperatures can be varied within a substantial range. In general, the process is carried out at temperatures between 0° C. and 250° C., preferably between 50° C. and 150° C.

Process (A) according to the invention is generally carried out under atmospheric pressure.

When carrying out process (A) according to the invention, the reactants of the formulae (II) and the deprotonating bases are generally employed in approximately equimolar amounts. However, it is also possible to use one or the other component in a larger excess (up to 3 mols).

Process (Bα) is characterized in that compounds of the formula (Ia) are reacted with carbonyl halides of the formula (III).

Diluents which can be employed in process (Bα) according to the invention in which the acyl halides are used, are all solvents which are inert towards these compounds. The following can preferably be used; hydrocarbons such as benzine, benzene, toluene, xylene and tetralin, furthermore halogenohydrocarbons such as methylene chloride, chloroform, carbon tetrachloride, chlorobenzene and o-dichlorobenzene, moreover ketones such as acetone and methyl isopropyl ketone, furthermore ethers such as diethyl ether, tetrahydrofuran and dioxane, in addition carboxylic esters such as ethyl acetate, and also strongly polar solvents such as dimethyl sulphoxide and sulpholane. If the stability of the acid halide to hydrolysis permits, the reaction can also be carried out in the presence of water.

If the corresponding carbonyl halides are used, then suitable acid-binding agents in the reaction according to process (Bα) according to the invention are all customary acid acceptors. The following can preferably be used: tertiary amines such as triethylamine, pyridine, diazabicyclooctane (DABCO), diazabicycloundecane (DBU), diazabicyclononene (DBN), Hüning base and N,N-dimethylaniline, furthermore alkaline earth metal oxides such as magnesium oxide and calcium oxide, moreover alkali metal carbonates and alkaline earth metal carbonates such as sodium carbonate, potassium carbonate and calcium carbonate.

When using carbonyl halides, too, in process (Bα) according to the invention, the reaction temperatures can also be varied within a substantial range. In general, the process is carried out at temperatures between $-20°$ C. and $+150°$ C., preferably between $0°$ C. and $100°$ C.

When carrying out process (Bα) according to the invention, the starting substances of the formula (Ia) and the carbonyl halide of the formula (III) are generally used in approximately equivalent amounts. However, it is also possible to employ the carboxylic anhydride in a larger excess (up to 5 mols). Working-up is carried out by customary methods.

Process (Bβ) is characterized in that compounds of the formula (Ia) are reacted with carboxylic hydrides of the formula (IV).

If, in process (Bβ) according to the invention, carboxylic anhydrides are used as the reactant of the formula (IV), the diluents which can preferably be used are those which are also preferably suitable when acid halides are used. Besides, a carboxylic hydride employed in excess can also simultaneously act as the diluent.

When carboxylic anhydrides are used, the reaction temperatures in process (Bβ) according to the invention can also be varied within a substantial range. In general, the process is carried out at temperatures between $-20°$ C. and $+150°$ C., preferably between $0°$ C. and $100°$ C.

When carrying out the process according to the invention, the starting substances of the formula (Ia) and the carboxylic anhydride of the formula (IV) are generally used in approximately equivalent amounts. However, it is also possible to employ the carboxylic anhydride in a larger excess (up to 5 mols). Working-up is carried out by customary methods.

In general, a procedure is followed in which the diluent and the carboxylic anhydride which is present in excess, as well as the carboxylic acid which is formed, are removed by distillation or by washing with an organic solvent or with water.

Process (C) is characterized in that compounds of the formula (Ia) are reacted with chloroformic esters or chloroformic thioesters of the formula (V).

If the corresponding chloroformic esters or chloroformic thioesters are used, then the acid-binding agents which are suitable in the reaction according to process (C) according to the invention are all customary acid acceptors. The following can preferably be used; tertiary amines, such as triethylamine, pyridine, DABCO, DBC, DBA, Hünig base and N,N-dimethyl-aniline, furthermore alkaline earth metal oxides such as magnesium oxide and calcium oxide, moreover alkali metal carbonates and alkaline earth metal carbonates such as sodium carbonate, potassium carbonate and calcium carbonate.

When the chloroformic esters or chloroformic thioesters are used, the diluents employed in process (C) according to the invention are all solvents which are inert towards these compounds. The following can preferably be used: hydrocarbons, such as benzine, benzene, toluene, xylene and tetralin, furthermore halogenohydrocarbons such as methylene chloride, chloroform, carbon tetrachloride, chlorobenzene and o-dichlorobenzene, moreover ketones such as acetone and methyl isopropyl ketone, furthermore ethers such as diethyl ether, tetrahydrofuran and dioxane, in addition carboxylic esters, such as ethyl acetate, and also strongly polar solvents such as dimethyl sulphoxide and sulpholane.

When the chloroformic esters or chloroformic thioesters are used as carboxylic acid derivatives of the formula (V), the reaction temperatures when carrying out process (C) according to the invention can be varied within a substantial range. If the process is carried out in the presence of a diluent and of an acid-binding agent, the reaction temperatures are generally between $-20°$ C. and $+100°$ C., preferably between $0°$ C. and $50°$ C.

Process (C) according to the invention is generally carried out under atmospheric pressure.

When carrying out process (C) according to the invention, the starting substances of the formula (Ia) and the corresponding chloroformic ester or chloroformic thioester of the formula (V) are generally used in approximately equivalent amounts. However, it is also possible to employ one or the other component in a larger excess (up to 2 mols). Working-up is then carried out by customary methods. In general, a procedure is followed in which precipitated salts are removed and the reaction mixture which remains is concentrated by stripping off the diluent.

In preparation process $D_α$, about 1 mol of chloromonothioformic ester or chlorodithioformic ester of the formula (VII) is reacted per mol of starting compound of the formula (Ia) at $0°$ to $120°$ C., preferably at $20°$ to $60°$ C.

Suitable diluents which may be added are all inert polar organic solvents such as ethers, amides, alcohols, sulphones or sulphoxides.

It is preferred to employ dimethyl sulphoxide, tetrahydrofuran, dimethylformamide or dimethyl sulphide.

If, in a preferred embodiment, the enolate salt of the compound (Ia) is prepared by adding strong deprotonating agents such as, for example, sodium hydride or potassium tertiary butylate, the further addition of acid-binding agents can be dispensed with.

If acid-binding agents are employed, then those which are suitable are inorganic or organic bases, sodium hydroxide, sodium carbonate, potassium carbonate, pyridine or triethylamine being mentioned by way of example.

The reaction can be carried out at atmospheric pressure or under increased pressure; it is preferably carried out at atmospheric pressure. Working-up is carried out by customary methods.

In preparation process $D_β$, the equimolar amount, or an excess, of carbon disulphide is added per mol of starting compound of the formula (II). This process is preferably carried out at temperatures of from $0°$ to $50°$ C. and, in particular, at $20°$ to $30°$ C.

Often, it is expedient to first prepare the corresponding salt from the compound of the formula (II) by adding a deprotonating agent (such as, for example, potassium tertiary butylate or sodium hydride). Compound (II) is reacted with carbon disulphide until the formation of the intermediate is complete, for example after stirring for several hours at room temperature.

Further reaction with the alkyl halide of the formula (VIII) is preferably carried out at $0°$ to $70°$ C. and, in particular, at $20°$ to $50°$ C. At least the equimolar amount of alkyl halide is employed in this process.

The process is carried out at atmospheric pressure or under increased pressure, preferably at atmospheric pressure.

Again, working-up is carried out by customary methods.

In preparation process E), about 1 mol of sulphonyl chloride (VIII) is reacted per mol of starting compound of the formula (Ia) at 0° to 150° C., preferably at 20° to 70° C.

Suitable diluents which are optionally added are all inert polar organic solvents such as ethers, amides, nitriles, alcohols, sulphones or sulphoxides.

It is preferred to employ dimethyl sulphoxide, tetrahydrofuran, dimethylformamide or dimethyl sulphide.

If, in a preferred embodiment, the enolate salt of the compound Ia is prepared by adding strong deprotonating agents (such as, for example, sodium hydride or potassium tertiary butylate), the further addition of acid-binding agents can be dispensed with.

If acid-binding agents are employed, then those which are suitable are customary inorganic or organic bases, sodium hydroxide, sodium carbonate, potassium carbonate or pyridine being mentioned by way of example.

The reaction can be carried out at atmospheric pressure or under increased pressure, the reaction preferably being carried out at atmospheric pressure. Working-up is carried out by customary methods.

If appropriate, preparation process E can be carried out under phase-transfer conditions (W. J. Spillane et al.; J. Chem. Soc., Perkin Trans I, (3) 677-9 (1982)). In this case, 0.3 to 1.5 mols of sulphenyl chloride VIII, preferably 0.5 mol, are reacted per mol of starting compound of the formula (Ia) at 0° to 150° C., preferably at 20° to 70° C.

Phase-transfer catalysts which can be used are all quaternary ammonium salts, preferably tetraoctylammonium bromide and benzyltriethylammonium chloride. In this case, all nonpolar inert solvents can act as the organic solvents, benzene and toluene preferably being employed.

To obtain compounds of the structure (Ie) in preparation process F 1 to 2, preferably 1 to 1.3, mols of the phosphorus compound of the formula (IX) is generally reacted per mol of the compound (Ia) at temperatures between -40° and 150° C., preferably between -10° and 110° C.

Suitable diluents which are optionally added are all inert, polar organic solvents such as ethers, amides, nitriles, alcohols, sulphides, sulphones, sulphoxides, etc.

It is preferred to employ acetonitrile, dimethyl sulphoxide, tetrahydrofuran, dimethylformamide or dimethyl sulphide.

Suitable acid-binding agents which are optionally added are customary inorganic or organic bases such as hydroxides or carbonates. The following may be mentioned by way of example: sodium hydroxide, sodium carbonate, potassium carbonate or pyridine.

The reaction can be carried out at atmospheric pressure or under increased pressure, the process preferably being carried out at atmospheric pressure. Workingup is carried out by customary methods of organic chemistry. The end products obtained are preferably purified by crystallization, chromatographic purification or by socalled "incipient distillation", i.e. removal of the volatile components in vacuo.

In preparation process G$_\alpha$, about 1 mol of isocyanate of the formula (X) is reacted per mol of starting compound of the formula Ia at 0° to 100° C., preferably at 20° to 50° C.

Suitable diluents which are optionally added are all inert organic solvents such as ethers, amides, nitriles, sulphones or sulphoxides.

If appropriate, it is possible to add catalysts to accelerate the reaction. Catalysts which can very advantageously be used are organotin compounds such as, for example, dibutyltin dilaurate. The process is preferably carried out at atmospheric pressure.

In preparation process G$_\beta$, about 1 mol of carbamoyl chloride or thiocarbamoyl chloride of the formula (XI) is reacted per mol of starting compound of the formula (Ia) at 0° to 150° C., preferably at 20° to 70° C.

Suitable diluents which are optionally added are all inert polar organic solvents such as ethers, amides, alcohols, sulphones or sulphoxides.

It is preferred to employ dimethyl sulphoxide, tetrahydrofuran, dimethylformamide or dimethyl sulphide.

If, in a preferred embodiment, the enolate salt of the compound Ia is prepared by adding strong deprotonating agents (such as, for example, sodium hydride or potassium tertiary butylate), the further addition of acid-binding agents can be dispensed with.

If acid-binding agents are employed, then those suitable are customary inorganic or organic bases, sodium hydroxide, sodium carbonate, potassium carbonate or pyridine being mentioned by way of example.

The reaction can be carried out at atmospheric pressure or under increased pressure, the reaction preferably being carried out under atmospheric pressure. Working-up is carried out by customary methods.

Process H is characterized in that compounds of the formula (Ia) are reacted with metal hydroxides (XII) or amines (XIII).

Diluents which can preferably be employed in the process according to the invention are ethers such as tetrahydrofuran, dioxane or diethyl ether, also alcohols such as methanol, ethanol or isopropanol, and also water. Process H according to the invention is generally carried out under atmospheric pressure. In general, the reaction temperatures are between -20° and 100° C., preferably between 0° and 50° C.

When carrying out process H according to the invention, the starting substances of the formula (Ia) or (XII) or (XIII) are generally used in approximately equimolar amounts. However, it is also possible to employ one or the other component in a larger excess (up to 2 mols). In general, a procedure is followed in which the reaction mixture is concentrated by stripping off the diluent.

EXAMPLE 1

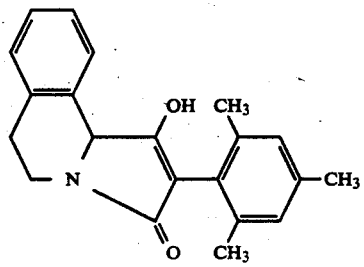

3.6 g (0.12 mol) of sodium hydride (suspension, 80%) are initially introduced into 60 ml of absolute toluene. 30.9 g (0.085 mol) of ethyl 1,2,7,8-tetrahydroisoquinoline-N-(2,4,6-trimethylphenyl-acetyl)-2-carboxylate, dissolved in 90 ml of absolute toluene, are added dropwise under reflux conditions and stirring of the mixture is continued together with thin-layer chromatography checking. When the reaction is complete, excess sodium hydride is destroyed with ethanol and the batch is evaporated on a rotary evaporator. The residue is taken up in water, the mixture is acidified at 0°-20° C. using concentrated hydrochloric acid, and the solids are filtered off with suction and dried in vacuo over $P_2O_5$. Purification is effected by boiling in methyl tert.-butyl ether/n-hexane. In this manner, 19.43 g (=71.1% of theory) of 1-aza-12-(2,4,6-trimethylphenyl)-tricyclo-(8,3,0$^{1.10}$,0$^{4.9}$)-tridecane-4,6,8-triene-11,13-dione of melting point 78° C. are obtained.

The following were obtained analogously:

TABLE 1

(Ia)

| Example No. | [A-N structure] | X | Y | $Z_n$ | m.p. °C. |
|---|---|---|---|---|---|
| 2 | [bicyclic] | Cl | Cl | H | >220 |
| 3 | [bicyclic] | Cl | H | 6-Cl | >220 |
| 4 | [bicyclic] | CH$_3$ | CH$_3$ | H | |
| 5 | [bicyclic] | CH$_3$ | H | 6-CH$_3$ | |
| 6 | [bicyclic] | CH$_3$ | CH$_3$ | 6-CH$_3$ | >230 |
| 7 | [tetrahydroquinoline] | CH$_3$ | CH$_3$ | 6-CH$_3$ | 151 |
| 8 | [decahydroquinoline] | CH$_3$ | CH$_3$ | 6-CH$_3$ | >230 |

TABLE 1-continued (Ia)

Structure: OH, X, A-N ring fused to central ring with C=O, bonded to phenyl bearing X, Y, $Z_n$.

A-N fragment shown separately.

| Example No. | A (structure) | X | Y | $Z_n$ | m.p. °C. |
|---|---|---|---|---|---|
| 9 | decahydroisoquinoline-N-methyl | CH₃ | CH₃ | 6-CH₃ | 204 |
| 10 | H₂C₂O-C(O)-N-pyrrolidine fused, N-methyl | CH₃ | CH₃ | 6-CH₃ | 146 |
| 11 | t-C₄H₉O-C(O)-N-pyrrolidine fused, N-methyl | CH₃ | CH₃ | 6-CH₃ | |
| 11a | H₃C-C(O)-N-pyrrolidine fused, N-methyl | CH₃ | CH₃ | 6-CH₃ | 165 |
| 11b | indoline, N-H | CH₃ | CH₃ | 6-CH₃ | >220 |
| 11c | tetrahydro-β-carboline, NH, N-methyl | CH₃ | CH₃ | 6-CH₃ | >220 |

EXAMPLE 12

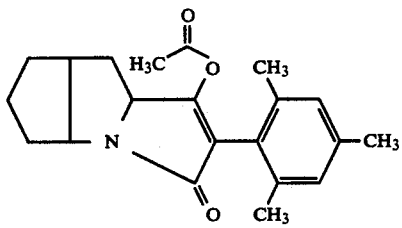

To 5.95 g (20 mmol) of 1-aza-tricyclo-(6,3,0$^{1.8}$,0$^{2.6}$)-10-(2,4,6-trimethylphenyl)-undecane-9,11-dione, suspended in 70 ml of methyl tert.-butyl ether, there are added 1.63 ml of absolute pyridine and 3.4 ml (20 mmol) of Hünig base. At 0°-10° C., 1.5 ml (20 mmol) of acetyl chloride in 5 ml of methyl tert.-butyl ether are added dropwise, stirring is continued for 15 minutes, the precipitate is filtered off, the solution is evaporated in vacuo on a rotary evaporator, and the residue is chromatographed on silica gel with cyclohexane/ethyl acetate 1:1. After crystallization from n-hexane, 4.7 g (=69.2% of theory) of 1-aza-9-acetoxytricyclo-(6,3,0$^{1.8}$,0$^{2.6}$)-10-(2,4,6-(trimethylphenyl)-9-undecane-11-one of melting point 100° C. were obtained.

The following are obtained analogously:

TABLE 2

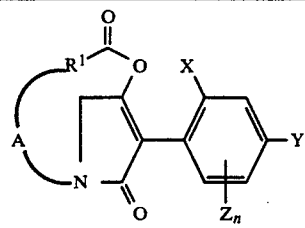

| Example No. | A︶N | X | Y | $Z_n$ | $R^1$ | m.p. °C. |
|---|---|---|---|---|---|---|
| 13 | (bicyclic N-methyl) | Cl | Cl | H | $CH_3-$ | 104 |
| 14 | " | Cl | Cl | H | $(CH_3)_3C-$ | Oil |
| 15 | " | Cl | H | 6-Cl | $CH_3-$ | 185 |
| 16 | " | Cl | H | 6-Cl | $(CH_3)_3C-$ | 132 |
| 17 | " | $CH_3$ | $CH_3$ | H | $CH_3-$ | |
| 18 | " | $CH_3$ | $CH_3$ | H | $(CH_3)_3C-$ | |
| 19 | " | $CH_3$ | H | 6-$CH_3$ | $CH_3-$ | |
| 20 | (bicyclic N-methyl) | $CH_3$ | H | 6-$CH_3$ | $(CH_3)_3C-$ | |
| 20a | " | $CH_3$ | $CH_3$ | 6-$CH_3$ | $CH_3CH_2-$ | |
| 21 | " | $CH_3$ | $CH_3$ | 6-$CH_3$ | $(CH_3)_2CH-$ | Oil |
| 22 | " | $CH_3$ | $CH_3$ | 6-$CH_3$ | $(CH_3)_3C-$ | 104 |
| 23 | " | $CH_3$ | $CH_3$ | 6-$CH_3$ | $CH_3-(CH_2)_3-$ | Oil |
| 23a | " | $CH_3$ | $CH_3$ | 6-$CH_3$ | $(CH_3)_2CH-CH_2-$ | Oil |
| 24 | " | $CH_3$ | $CH_3$ | 6-$CH_3$ | $C_2H_5-C(CH_3)_2-$ | Oil |
| 25 | " | $CH_3$ | $CH_3$ | 6-$CH_3$ | $(CH_3)_3C-CH_2-$ | Oil |
| 26 | " | $CH_3$ | $CH_3$ | 6-$CH_3$ | $(CH_3)_2CH-C(CH_3)_2-$ | 98 |
| 27 | " | $CH_3$ | $CH_3$ | 6-$CH_3$ | $CH_2=CH-(CH_2)_8-$ | Oil |
| 27a | " | $CH_3$ | $CH_3$ | 6-$CH_3$ | $C_{17}H_{35}-$ | Oil |
| 28 | " | $CH_3$ | $CH_3$ | 6-$CH_3$ | $Cl-C(CH_3)(CH_3)-CH_2-$ | 102 |
| 29 | (bicyclic N-methyl) | $CH_3$ | $CH_3$ | 6-$CH_3$ | $Cl-C(CH_3)(CH_2Cl)-$ | |
| 30 | " | $CH_3$ | $CH_3$ | 6-$CH_3$ | $H_3C-O-C(CH_3)(CH_3)-$ | Oil |

TABLE 2-continued
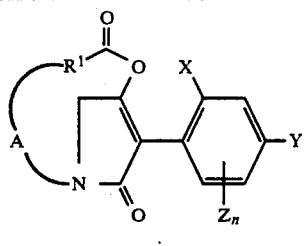
| Example No. |  A | X | Y | $Z_n$ | $R^1$ | m.p. °C. |
|---|---|---|---|---|---|---|
| 31 | " | CH₃ | CH₃ | 6-CH₃ | H₃C—O—C(CH₃)—CH₂—O—CH₃ (with CH₃) | Oil |
| 32 | " | CH₃ | CH₃ | 6-CH₃ | H₃C\C=CH—CH₃ / H₃C | 120 |
| 33 | " | CH₃ | CH₃ | 6-CH₃ | H₃C—S—CH₂ | |
| 34 | " | CH₃ | CH₃ | 6-CH₃ | dioxane-CH₃ | 121 |
| 34a | bicyclic N | CH₃ | CH₃ | 6-CH₃ | cyclohexyl-propyl | Oil |
| 34b | " | CH₃ | CH₃ | 6-CH₃ | CH₃O—C(=O)—CH₂CH₂CH₂ | 113 |
| 34c | " | CH₃ | CH₃ | 6-CH₃ | Cl—C₆H₄—CH₂CH₂ | Oil |
| 35 | bicyclic N | CH₃ | CH₃ | 6-CH₃ | dioxane-C₂H₅ | 125 |
| 35a | bicyclic N | CH₃ | CH₃ | 6-CH₃ | C₆H₅ | 69 |
| 35b | " | CH₃ | CH₃ | 6-CH₃ | 2-Cl-C₆H₄ | Oil |

TABLE 2-continued
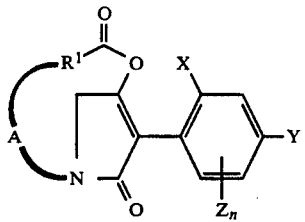
| Example No. | A-N | X | Y | $Z_n$ | $R^1$ | m.p. °C. |
|---|---|---|---|---|---|---|
| 35c | " | CH₃ | CH₃ | 6-CH₃ | 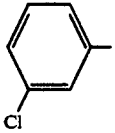 | resin |
| 35d | " | CH₃ | CH₃ | 6-CH₃ | 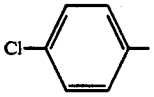 | 125 |
| 36 | " | CH₃ | CH₃ | 6-CH₃ | 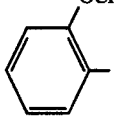 | 75 |
| 37 | 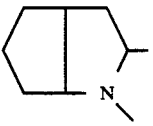 | CH₃ | CH₃ | 6-CH₃ | 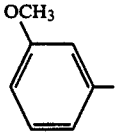 | 83 |
| 38 | " | CH₃ | CH₃ | 6-CH₃ | 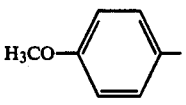 | 146 |
| 39 | 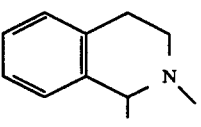 | CH₃ | CH₃ | 6-CH₃ | CH₃— | 194 |
| 40 |  | CH₃ | CH₃ | 6-CH₃ | (CH₃)₃C— | |
| 41 | 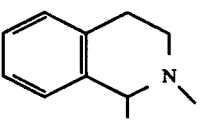 | CH₃ | CH₃ | 6-CH₃ | CH₃— | resin |
| 42 | " | CH₃ | CH₃ | 6-CH₃ | (CH₃)₃C— | 153 |
| 43 | 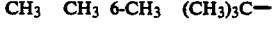 | CH₃ | CH₃ | 6-CH₃ | CH₃— | |

TABLE 2-continued

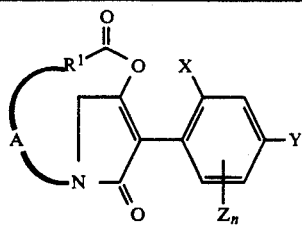

| Example No. | A structure | X | Y | $Z_n$ | $R^1$ | m.p. °C. |
|---|---|---|---|---|---|---|
| 44 | " | $CH_3$ | $CH_3$ | 6-$CH_3$ | $(CH_3)_3C-$ | |
| 45 | decahydroquinoline (2-methyl, N-methyl) | $CH_3$ | $CH_3$ | 6-$CH_3$ | $CH_3-$ | 170 |
| 46 | decahydroquinoline (2-methyl, N-methyl) | $CH_3$ | $CH_3$ | 6-$CH_3$ | $(CH_3)_3C-$ | 148 |
| 47 | $H_5C_2O$-carbonyl piperidine with N-methyl pyrrolidine | $CH_3$ | $CH_3$ | 6-$CH_3$ | $CH_3-$ | Oil |
| 48 | " | $CH_3$ | $CH_3$ | 6-$CH_3$ | $(CH_3)_3C-$ | Oil |
| 48a | $H_3C$-acetyl piperidine with N-methyl pyrrolidine | $CH_3$ | $CH_3$ | 6-$CH_3$ | $CH_3-$ | 180 |
| 48b | indoline (2-methyl, N-methyl) | $CH_3$ | $CH_3$ | 6-$CH_3$ | $(CH_3)_3C-$ | 90 |

EXAMPLE 49

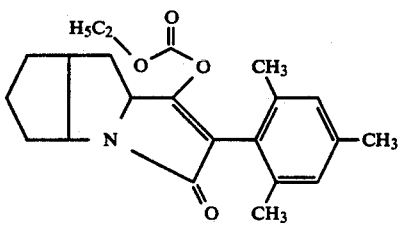

To 5.95 g (20 mmol) of 1-aza-tricyclo-(6,3,0$^{1.8}$,0$^{2.6}$)-10-(2,4,6-trimethylphenyl)-undecane-9,11-dione, suspended in 70 ml of methyl tert.-butyl ether, there are added 1.63 ml of absolute pyridine and 3.4 ml (20 mmol) of Hünig base. At 0°–10° C., 2 ml (20 mmol) of ethyl chloroformate in 5 ml of methyl tert.-butyl ether are added dropwise, stirring is continued for 15 minutes, the precipitate is filtered off, the solution is evaporated in vacuo on a rotary evaporator, and the residue is chromatographed on silica gel with cyclohexane/ethyl acetate 1:1. 6.1 g (=82.5% of theory) of 1-aza-9-ethoxycarbonyloxy-tricyclo-(6,3,0$^{1.8}$,0$^{2.6}$)-10-(2,4,6-trimethylphenyl)-9-undecane-11-one are obtained as a yellow oil.

The following are obtained analogously:

TABLE 3

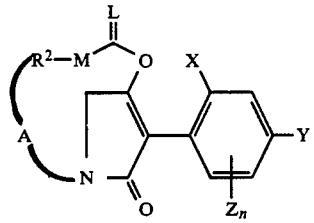
(Ic)

| Ex. No. |  | X | Y | $Z_n$ | L | M | $R^2$ | m.p. °C. |
|---|---|---|---|---|---|---|---|---|
| 50 | (bicyclic) | Cl | Cl | H | O | O | $C_2H_5-$ | 89 |
| 50a | " | Cl | Cl | H | O | O | $(CH_3)_2CH-$ | 100 |
| 50b | " | Cl | Cl | H | O | O | $CH_3CH_2-CH(CH_3)-$ | Oil |
| 51 | " | Cl | H | 6-Cl | O | O | $C_2H_5-$ | 98 |
| 51a | " | Cl | H | 6-Cl | O | O | $(CH_3)_2CH-$ | 132 |
| 51b | " | Cl | H | 6-Cl | O | O | $CH_3CH_2-CH(CH_3)-$ | 65 |
| 52 | (bicyclic) | $CH_3$ | $CH_3$ | H | O | O | $C_2H_5-$ | |
| 53 | " | $CH_3$ | H | 6-$CH_3$ | O | O | $C_2H_5-$ | |
| 54 | " | $CH_3$ | $CH_3$ | 6-$CH_3$ | O | O | $CH_3-$ | Oil |
| 55 | " | $CH_3$ | $CH_3$ | 6-$CH_3$ | O | O | $(CH_3)_2CH-$ | 104 |
| 56 | (bicyclic) | $CH_3$ | $CH_3$ | 6-$CH_3$ | O | O | $(CH_3)_2CH-CH_2-$ | 78 |
| 57 | " | $CH_3$ | $CH_3$ | 6-$CH_3$ | O | O | $C_2H_5-CH(CH_3)-$ | 82 |
| 58 | " | $CH_3$ | $CH_3$ | 6-$CH_3$ | O | O | $(CH_3)_3C-$ | 154 |
| 59 | " | $CH_3$ | $CH_3$ | 6-$CH_3$ | O | O | $(CH_3)_3CH-CH_2-$ | 107 |
| 60 | " | $CH_3$ | $CH_3$ | 6-$CH_3$ | O | O | cyclohexyl- | Oil |
| 60a | " | $CH_3$ | $CH_3$ | 6-$CH_3$ | O | O | $CH_2=CH-CH_2-$ | Oil |
| 61 | " | $CH_3$ | $CH_3$ | 6-$CH_3$ | O | O | $C_2H_5O-CH_2CH_2CH_2-$ | Oil |
| 62 | " | $CH_3$ | $CH_3$ | 6-$CH_3$ | O | O | $C_2H_5O-CH_2CH_2-O-CH_2-$ | Oil |

TABLE 3-continued

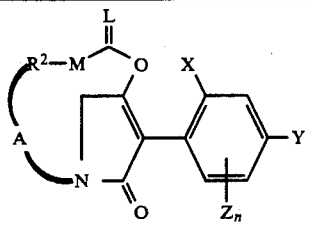

(Ic)

| Ex. No. | A–N | X | Y | $Z_n$ | L | M | $R^2$ | m.p. °C. |
|---|---|---|---|---|---|---|---|---|
| 63 | " | CH₃ | CH₃ | 6-CH₃ | O | O | –CH₂–C₆H₅ | Oil |
| 63a | (bicyclic N structure) | CH₃ | CH₃ | 6-CH₃ | O | O | –CH₂–CH₂–C₆H₅ | Oil |
| 63b | " | CH₃ | CH₃ | 6-CH₃ | O | O | C₂H₅O–CH(CH₃)– | Oil |
| 63c | " | CH₃ | CH₃ | 6-CH₃ | O | O | C₃H₇O–CH(CH₃)– | Oil |
| 63d | " | CH₃ | CH₃ | 6-CH₃ | O | O | (CH₃)₂CHO–CH(CH₃)– | Oil |
| 63e | " | CH₃ | CH₃ | 6-CH₃ | O | O | C₂H₅O–CH(C₂H₅)– | Oil |

PREPARATION/EXAMPLE NO. 64

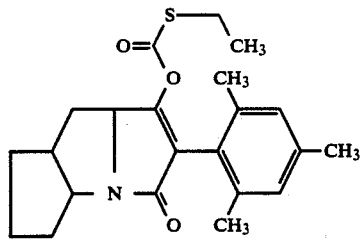

2.97 g of 1-aza-tricyclo-(6.3.0$^{1.8}$0$^{2.6}$)-10-(2,4,6-trimethylphenyl)-undecane-9,11-dione and 20 ml of absolute dimethyl formamide are treated with 0.3 g of sodium hydride (80%). After the end of the hydrogen formation the mixture is cooled to 10° C. and 1.5 ml (0.014 mol) of

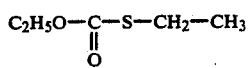

are added. Then stirring is carried out for several hours, the mixture is added to 100 ml of water, then it is extracted three times with methylene chloride and it is washed once with 40 ml of 40% hydrochloric acid, it is dried with sodium sulphate and evaporated.

Yield: 2.73 g (71% of theory) of the illustrated compound, melting point: 112° C.

PREPARATION/EXAMPLE NO. 64c

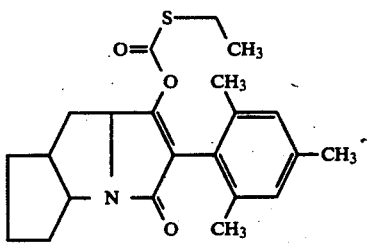

2.97 g (0.01 mol) of 1-aza-tricyclo-(6,3,0$^{1.8}$0$^{2.6}$)-10-(2,4,6-trimethylphenyl)-undecane-9,11-dione and 20 ml of absolute dimethylformamide are treated with 0.3 g of sodium hydride (80%). After the end of the hydrogen formation, 3 ml (0.01 mol) of carbon disulphide are added and stirring is carried out for 3 hours at room temperature. Furthermore 3 ml (0.05 mol) of methyl iodide are added and stirring is carried out for several hours at room temperature. Finally the mixture is added to 100 ml of water, extracted three times with methylene chloride it is dried over sodium sulphate and evaporated.

Yield: 1.77 g of the illustrated compound (64% of theory).

Melting point: 90°–91° C.

PREPARATION/EXAMPLE NO. 72

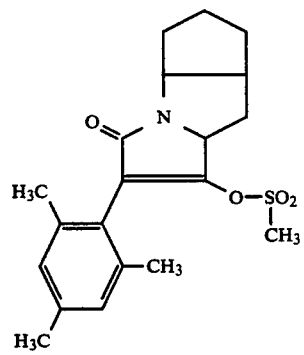

3.56 g of 1-aza-tricyclo-(6,3,0$^{1.8}$0$^{2.6}$)-10-(2,4,6-trimethylphenyl)-undecane-9,11-dione and 20 ml of absolute dimethyl formamide are treated with 0.3 g of sodium hydride (80%). After the end of the hydrogen formation it is cooled to 10° C. and 1.6 g (0.014 mol) of meth- TABLE 3
(continuation)

| Ex. No. | A-N structure | X | Y | $Z_n$ | L | M | $R^2$ | m.p. °C. |
|---|---|---|---|---|---|---|---|---|
| 64 | bicyclic fused cyclopentane/pyrrolidine with N-CH$_3$ | CH$_3$ | CH$_3$ | 6-CH$_3$ | O | S | C$_2$H$_5$— | 112 |
| 64a | " | CH$_3$ | CH$_3$ | 6-CH$_3$ | O | S | CH$_3$—(CH$_2$)$_3$— | Oil |
| 64b | " | CH$_3$ | CH$_3$ | 6-CH$_3$ | O | S | phenethyl | 105 |
| 64c | " | CH$_3$ | CH$_3$ | 6-CH$_3$ | S | S | CH$_3$— | 90–91 |
| 64d | " | CH$_3$ | CH$_3$ | 6-CH$_3$ | S | S | C$_2$H$_5$— | 94–95 |
| 64e | " | CH$_3$ | CH$_3$ | 6-CH$_3$ | S | S | (CH$_3$)$_2$CH— | 80–81 |
| 65 | tetrahydroisoquinoline N-CH$_3$ | CH$_3$ | CH$_3$ | 6-CH$_3$ | O | O | C$_2$H$_5$— | |
| 66 | " | CH$_3$ | CH$_3$ | 6-CH$_3$ | O | O | (CH$_3$)$_2$CH— | |
| 67 | " | CH$_3$ | CH$_3$ | 6-CH$_3$ | O | O | (CH$_3$)$_3$C—CH$_2$— | |
| 68 | decahydroisoquinoline N-CH$_3$ | CH$_3$ | CH$_3$ | 6-CH$_3$ | O | O | C$_2$H$_5$— | |
| 69 | " | CH$_3$ | CH$_3$ | 6-CH$_3$ | O | O | (CH$_3$)$_2$CH— | |
| 70 | tetrahydroquinoline | CH$_3$ | CH$_3$ | 6-CH$_3$ | O | O | C$_2$H$_5$— | | ane sulphonic acid chloride are added. Then stirring is carried out at room temperature for one hour. The mixture is stirred into 100 ml of water, it is extracted three times with methylene chloride, it is washed once with 40 ml of 5% hydrochloric acid, it is dried over sodium sulphate and evaporated.

Yield: 2.80 g (75% of theory) of the illustrated compound.

Melting point: 140° C.

TABLE 3
(continuation)

| Ex. No. | (structure) | X | Y | $Z_n$ | L | M | $R^2$ | m.p. °C. |
|---|---|---|---|---|---|---|---|---|
| 71 | tetrahydroquinoline | CH₃ | CH₃ | 6-CH₃ | O | O | (CH₃)₂CH— | |
| 72 | decahydroquinoline | CH₃ | CH₃ | 6-CH₃ | O | O | C₂H₅— | |
| 73 | " | CH₃ | CH₃ | 6-CH₃ | O | O | (CH₃)₂CH— | |
| 74 | H₅C₂O-C(O)-N-piperidine | CH₃ | CH₃ | 6-CH₃ | O | O | C₂H₅— | |
| 75 | " | CH₃ | CH₃ | 6-CH₃ | O | O | (CH₃)₂CH— | Oil |
| 76 | " | CH₃ | CH₃ | 6-CH₃ | O | O | C₂H₅—CH—<br>\|<br>CH₃ | Oil |
| 76a | H₃C-C(O)-N-piperidine | CH₃ | CH₃ | 6-CH₃ | O | O | CH₃ | 180 |

TABLE 4

(Id)

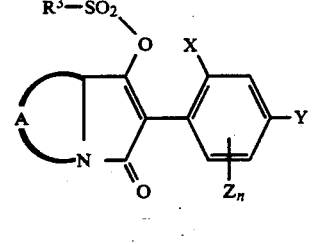

| Ex. No. | (structure) | X | Y | $Z_n$ | $R^3$ | m.p. °C. |
|---|---|---|---|---|---|---|
| 77 | bicyclic | CH₃ | CH₃ | 6-CH₃ | CH₃— | 149 |

TABLE 4-continued (Id)

Structure: R³—SO₂—O on ring with A-N, carbonyl, connected to phenyl with X, Y, Zn substituents.

| Ex. No. | A-N group | X | Y | Zn | R³ | m.p. °C. |
|---|---|---|---|---|---|---|
| 78 | " | CH₃ | CH₃ | 6-CH₃ | phenethyl (–CH₂CH₂–C₆H₅) | |
| 79 | " | CH₃ | CH₃ | 6-CH₃ | 4-Cl-C₆H₄–CH₂CH₂– | |
| 80 | " | CH₃ | CH₃ | 6-CH₃ | phenyl (C₆H₅–) | |
| 81 | " | CH₃ | CH₃ | 6-CH₃ | 4-Cl-C₆H₄– | |

TABLE 5

(Ie)

Structure with R⁵, R⁴, L=P, O linking to ring with A-N, carbonyl, phenyl with X, Y, Zn.

| Example No. | A-N group | X | Y | Zn | L | R⁴ | R⁵ | m.p. |
|---|---|---|---|---|---|---|---|---|
| 82 | octahydroindole-type bicyclic N | CH₃ | CH₃ | 6-CH₃ | S | CF₃CH₂O— | CH₃ | |
| 83 | " | CH₃ | CH₃ | 6-CH₃ | S | C₂H₅—O— | C₃H₇—S— | |
| 84 | " | CH₃ | CH₃ | 6-CH₃ | O | CH₃—O— | C₂H₅—S— | |
| 85 | " | CH₃ | CH₃ | 6-CH₃ | O | CH₃—O— | (CH₃)₂CH—S— | |
| 86 | " | CH₃ | CH₃ | 6-CH₃ | O | CH₃—O— | C₂H₅–CH(CH₃)–S— | |

PREPARATION/EXAMPLE NO. 87 a up in the usual manner. The purification is effected by filtering off on a silica gel frit (toluene:acetone 8:2).

Yield: 8.20 g of the illustrated compound (52% of theory).

$n_D^{20} = 1.5600$.

TABLE 5
continuation

| Ex. No. | (A-N ring) | X | Y | $Z_n$ | L | $R^4$ | $R^5$ | m.p. |
|---|---|---|---|---|---|---|---|---|
| 87 | (bicyclic structure) | $CH_3$ | $CH_3$ | 6-$CH_3$ | O | $C_2H_5O-$ | $C_2H_5-S-$ | |
| 87a | " | $CH_3$ | $CH_3$ | 6-$CH_3$ | O | $C_2H_5-O-$ | $C_2H_7-S-$ | $n_D^{20}$: 1.560 |
| 88 | " | $CH_3$ | $CH_3$ | 6-$CH_3$ | O | $C_2H_5-O-$ | $(CH_3)_2CH-S-$ | |
| 89 | " | $CH_3$ | $CH_3$ | 6-$CH_3$ | O | $C_2H_5-O-$ | $C_2H_5\diagdown CH-S-$ / $CH_3$ | |
| 89a | " | $CH_3$ | $CH_3$ | 6-$CH_3$ | S | $CH_3$ | $CH_3-O-$ | 128 |
| 89b | " | $CH_3$ | $CH_3$ | 6-$CH_3$ | S | $C_2H_5$ | $CH_3-O-$ | 128 |
| 89c | " | $CH_3$ | $CH_3$ | 6-$CH_3$ | S | $CH_3$ | $C_2H_5-S-$ | Oil |
| 89d | " | $CH_3$ | $CH_3$ | 6-$CH_3$ | S | $CH_3$ | $C_3H_7-S-$ | 109 |
| 89e | " | $CH_3$ | $CH_3$ | 6-$CH_3$ | S | $CH_3$ | $(CH_3)_2CH-S-$ | $n_D^{20}$: 1.581 |
| 89f | (bicyclic structure) | $CH_3$ | $CH_3$ | 6-$CH_3$ | S | $CH_3$ | allyl-S- | 79 |
| 89g | " | $CH_3$ | $CH_3$ | 6-$CH_3$ | S | $CH_3$ | $C_4H_9-S-$ | 88 |
| 89h | " | $CH_3$ | $CH_3$ | 6-$CH_3$ | S | $CH_3$ | $(CH_3)_2CH-CH_2-S-$ | 91 |
| 89i | " | $CH_3$ | $CH_3$ | 6-$CH_3$ | S | $CH_3$ | $(CH_3)_3C-S-$ | $n_D^{20}$: 1.568 |
| 89j | " | $CH_3$ | $CH_3$ | 6-$CH_3$ | S | $CH_3$ | $CH_3-(CH_2)_4-S-$ | Oil |
| 89k | " | $CH_3$ | $CH_3$ | 6-$CH_3$ | S | $CH_3$ | $(CH_3)_2CH-(CH_2)_2-S-$ | Oil |
| 89l | " | $CH_3$ | $CH_3$ | 6-$CH_3$ | S | $C_2H_5$ | $C_2H_5-S-$ | 65 |
| 89m | " | $CH_3$ | $CH_3$ | 6-$CH_3$ | S | $C_2H_5$ | $(CH_3)_2CH-S-$ | $n_D^{20}$: 1.573 |
| 89n | " | $CH_3$ | $CH_3$ | 6-$CH_3$ | S | $C_2H_5$ | $CH_3(CH_2)_3-S-$ | $n_D^{20}$: 1.5634 |
| 89o | " | $CH_3$ | $CH_3$ | 6-$CH_3$ | S | $C_2H_5$ | $(CH_3)_3C-$ | 104 |

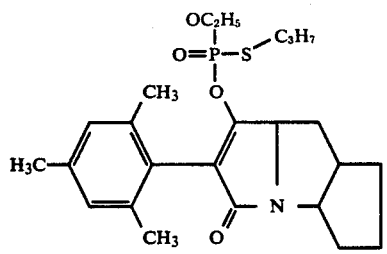

6.5 g (0.034 mol) of the compound

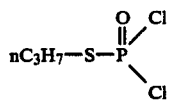

are added to 100 ml of toluene and treated with 5.2 ml (0.037 mol) of triethylamine. Then 1.6 g of ethanol (0.034 mol) in 10 ml of toluene are added dropwise at −5° C. to 0° C. It is stirred 2 hours at room temperature. Then 5.2 ml of triethylamine are added dropwise and 10 g of 1-aza-tricyclo-(6.3-0$^{1.8}$, 0$^{2.6}$)-10-(2,4,6-trimethylphenyl)-undecane-9,11-dione are added and worked

PREPARATION/EXAMPLE NO. 90

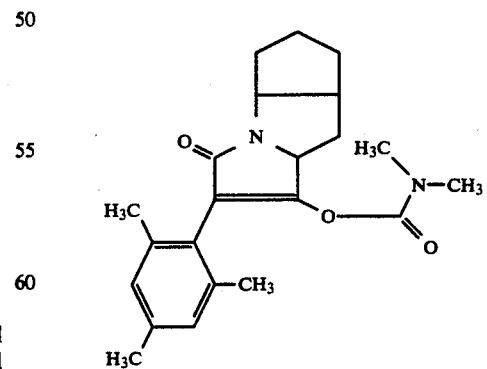

3.56 g of 1 aza-tricyclo-(6.3.0.$^{1.8}$,0$^{2.6}$)-10-(2.4.6-trimethylphenyl)-undecane-9,11-dione and 15 ml of absolute dimethyl formamide are treated with 0.3 g of sodium hydride (80%). After the end of the hydrogen formation it is cooled to 10° C. and 1.6 g of N,N-dimethyl carbamide acid chloride are added. Then stirring is carried out for one hour. The reaction product is stirred into 35 ml of 1% sodium hydroxide, it is extracted three times with methylene chloride, it is washed once with 15% hydrochloric acid and it is dried over sodium sulphate and evaporated.

Yield: 1.37 g (39% of theory) of the illustrated compound.

Melting point: 149° C.

TABLE 6

| Example No. | ⌒A⌒N\ | X | Y | $Z_n$ | L | $R^6$ | $R^7$ | m.p. |
|---|---|---|---|---|---|---|---|---|
| 90 | (bicyclic structure) | $CH_3$ | $CH_3$ | 6-$CH_3$ | O | $CH_3-$ | $CH_3-$ | 149 |
| 91 | " | $CH_3$ | $CH_3$ | 6-$CH_3$ | S | $CH_3-$ | $CH_3-$ | 78 |
| 92 | " | $CH_3$ | $CH_3$ | 6-$CH_3$ | O | $CH_2=CHCH_2-$ | $CH_2=CH-CH_2-$ | |
| 93 | " | $CH_3$ | $CH_3$ | 6-$CH_3$ | O | $-(CH_2)_2-O-(CH_2)_2-$ | | |
| 94 | " | $CH_3$ | $CH_3$ | 6-$CH_3$ | S | $-(CH_2)_5-$ | | |
| 95 | " | $CH_3$ | $CH_3$ | 6-$CH_3$ | S | | $C_2H_5-$ (phenyl) | |

TABLE 7

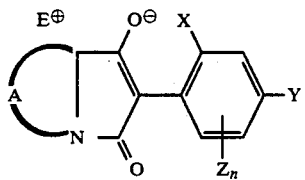

| Example No. | (If) | | | |
|---|---|---|---|---|
| | X | Y | $Z_n$ | $E^⊕$ |

EXAMPLE 96

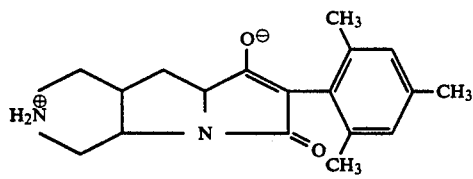

7.41 g (20 mmol) of 1,4-diaza-4-N-(ethoxycarbonyl)-tricyclo-(6,3,0^{1.8},0^{2.6})-10-(2,4,6-trimethylphenyl)-undecane-9,11-dione together with 15.78 g (50 mmol) of barium hydroxide octahydrate are refluxed in 100 ml of water for 10 hours. After the mixture has cooled, 6,9 g (50 mmol) of potassium carbonate are added in portions. After 15 minutes, the solids are filtered off with suction and rinsed with 20 ml of water, and the filtrate is adjusted to pH 7 using 1 N hydrochloric acid. The solids are again filtered off with suction and dried in vacuo. In this manner, 5.18 g (=86.9% of theory) of the inner salt of the above structure of melting point >230° C. are obtained as colorless powder.

| | ⌒A⌒N\ | X | Y | $Z_n$ | |
|---|---|---|---|---|---|
| 97 | (bicyclic structure) | $CH_3$ | $CH_3$ | 6-$CH_3$ | $Na^⊕$ |
| 98 | " | $CH_3$ | $CH_3$ | 6-$CH_3$ | $NH_4^⊕$ |
| 99 | " | $CH_3$ | $CH_3$ | 6-$CH_3$ | $H,CH_3 \backslash N^⊕ / H,CH_3$ |

INTERMEDIATES
EXAMPLE: 1A

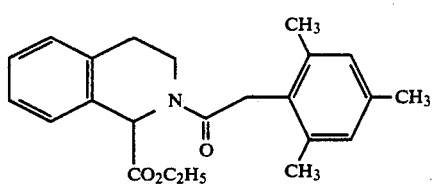

17.4 g (85 mmol) of ethyl 1,2,7,8-tetrahydroisoquinoline-2-carboxylate are initially introduced into 130 ml of absolute tetrahydrofuran, 11.9 ml (85 mmol) of triethylamine are added, and, at 0° to 10° C., 16.7 g (85 mmol) of mesityleneacetyl chloride are added dropwise. After 30 minutes, the mixture is stirred into 400 ml of ice-water and 100 ml of 1N hydrochloric acid, the batch is extracted with methylene chloride, and the extract is dried and evaporated in vacuo on a rotary evaporator. 30.9 g (=99.5% of theory) of ethyl 1,2,7,8-tetrahydroisoquinolin-N-(2,4,6-trimethylphenyl-acetyl)-2-carboxylate are obtained as a yellow oil.

The following were prepared analogously:

| Ex. No. | structure | X | Y | $Z_n$ | $R^8$ | m.p. °C. |
|---|---|---|---|---|---|---|
| 2A | | $CH_3$ | $CH_3$ | 6-$CH_3$ | $C_2H_5$ | Oil |
| 3A | | $CH_3$ | $CH_3$ | 6-$CH_3$ | $C_2H_5$ | Oil |
| 4A | | $CH_3$ | $CH_3$ | 6-$CH_3$ | $C_2H_5$ | Oil |
| 5A | | $CH_3$ | $CH_3$ | 6-$CH_3$ | $C_2H_5$ | Oil |
| 6A | | $CH_3$ | $CH_3$ | 6-$CH_3$ | $C_2H_5$ | Oil |

The following were prepared analogously:

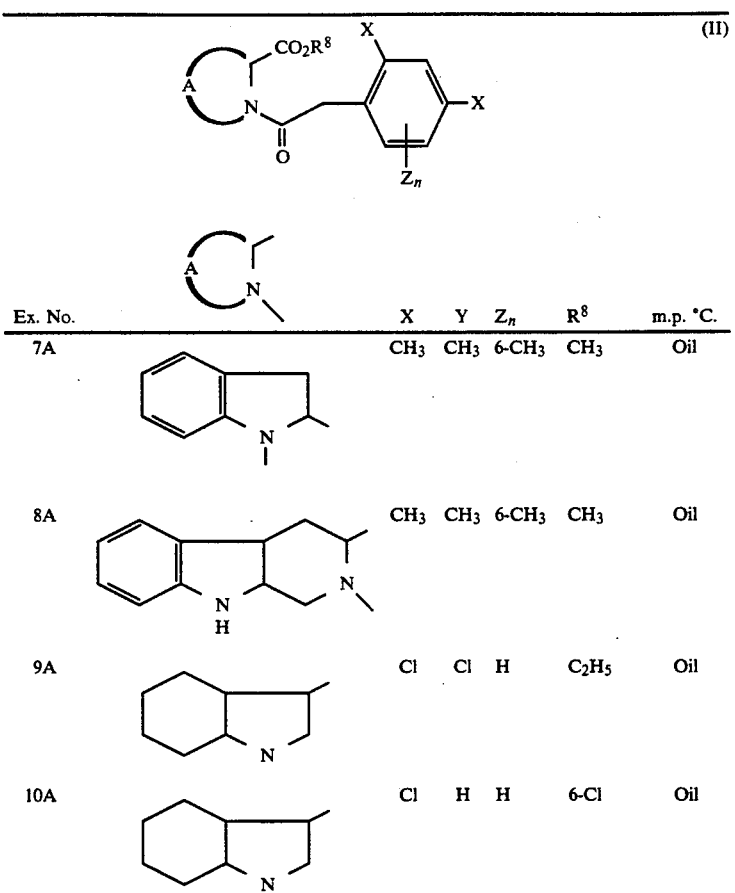

| Ex. No. | | X | Y | $Z_n$ | $R^8$ | m.p. °C. |
|---|---|---|---|---|---|---|
| 7A | (2-methylindoline) | $CH_3$ | $CH_3$ | 6-$CH_3$ | $CH_3$ | Oil |
| 8A | (tetrahydro-β-carboline derivative) | $CH_3$ | $CH_3$ | 6-$CH_3$ | $CH_3$ | Oil |
| 9A | (octahydroindole) | Cl | Cl | H | $C_2H_5$ | Oil |
| 10A | (octahydroindole) | Cl | H | H | 6-Cl | Oil |

The active compounds are suitable for combating animal pests, in particular insects and arachnids, encountered in agriculture, in forestry, in the protection of stored products and of materials, and in the hygiene field, and have good plant tolerance and favorable toxicity to warm-blooded animals. They are active against normally sensitive and resistant species and against all or some stages of development. The above-mentioned pests include:

From the order of the Isopoda, for example, *Oniscus asellus, Armadillidium vulgare* and *Porcellio scaber*. From the order of the Diplopoda, for example, *Blaniulus guttulatus*. From the order of the Chilopoda, for example, *Geophilus carpophagus* and Scutigera spec. From the order of the Symphyla, for example, *Scutigerella immaculata*. From the order of the Thysanura, for example, *Lepisma saccharina*. From the order of the Collembola, for example, *Onychiurus armatus*.

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria*. From the order of the Dermaptera, for example, *Forficula auricularia*. From the order of the Isoptera, for example, Reticulitermes spp.. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp.

From the order of the Thysanoptera, for example, *Hercinothrips femoralis* and *Thrips tabaci*. From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Bruchidius obtectus, Acanthoscelides obtectus, Hylotrupes bajulus,*

*Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp. From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus sppl., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active compounds according to the invention are not only active against plant, hygiene and stored product pests, but also, in the veterinary medicine sector, against animal parasites (ectoparasites and endoparasites), such as scaly ticks, argasidae, scab mites, trombidae, flies (stinging and licking), parasitic fly larvae, lice, hair lice, bird lice, fleas and worms which live as endoparasites.

The active compounds according to the invention can furthermore be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

It is characteristic of the compounds according to the invention that they have a selective activity against monocotyledon weeds in the pre- and the post-emergence method while being well tolerated by crop plants.

The active compounds according to the invention can be used, for example, in connection with the following plants:

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

Here, the active compounds according to the invention show a good tolerance by important crop plants such as, for example, wheat, cotton, soy beans, citrus fruit and sugar beets, while having an outstanding action against harmful plants, and they can therefore be employed as selective weed killers.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure and/or solid carriers, optionally with the use of surface-active agents, that is emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene, or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellant, such as halogenohydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, attractants, sterilizing agents, acaricides, nematicides, herbicides or fungicides. The insecticides include, for example, phosphoric esters, carbamates, carboxylic esters, chlorinated hydrocarbons, phenylureas and substances produced by microorganisms, inter alia.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

EXAMPLE A

Tetranychus test (resistent)
Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (Phaseolus vulgaris) which are heavily infested with all development stages of the common spider mite or two-spotted spider mite (Tetranychus urticae) are treated by being dipped into the active compound preparation of the desired concentration.

After the desired period of time, the destruction in % is determined. 100% denotes that all spider mites have been destroyed; 0% denotes that no spider mites have been destroyed.

In this test, a superior activity compared with the prior art is shown, for example, by the following compounds of the preparation examples: (6), (12), (22), (25), (47), (48), (49).

EXAMPLE B

Nephotettix test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Rice seedlings (Oryza sativa) are treated by being dipped into the active compound preparation of the desired concentration and infested with larvae of the green rice leaf hopper (Nephotettix cincticeps) while the seedlings are still moist.

After the desired period of time, the destruction in % is determined. 100% denotes that all cicadas were destroyed; 0% denotes that no cicadas were destroyed.

In this test, a superior activity compared with the prior art is shown, for example, by the following compounds of the preparation examples: (6), (12), (22), (25), (47), (48), (49).

EXAMPLE C

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, a superior activity compared with the prior art is shown, for example, by the following compounds of the preparation examples: (6), (10), (12), (22), (49).

EXAMPLE D

Post-emergence test
Solvent: 5 parts by weight of acetone
Emulsifier: 1 part by weight of alkylaryl polyglycol ether To prepare a suitable preparation of active compound, 1 part by weight of active compound was mixed with the stated amount of solvent, the stated amount of emulsifier was added, and the concentrate was diluted with water to the desired concentration.

Test plants which have a height of 5-15 cm are sprayed with the active compound preparation in such a way that the specifically desired amounts of active compound are applied per unit area. The concentration of the spray liquor is so chosen that the specifically desired amounts of active compound are applied in 2000 l of water/ha. After three weeks, the degree of damage to the plants is rated in % damage compared to the development of the untreated control.

The figures denote:
0% = no action (like untreated control)
100% = total destruction In this test, a superior activity compared with the prior art is shown, for example, by the following compounds of the preparation examples: (6), (10), (12), (22), (49).

It will be understood that the specification and examples are illustrative but not limitative of the present invention and that other embodiments within the spirit and scope of the invention will suggest themselves to those skilled in the art.

What is claimed is:

1. A polycyclic 3-arylpyrrolidine-2,4-dione derivative of the formula

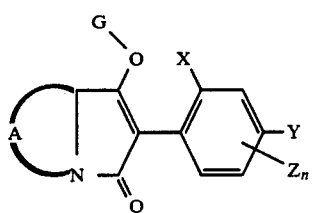

(I)

in which
A represents the radical of a bicyclic system wherein the pyrrolidine nitrogen is the sole heteroatom in the resulting tricyclic system,
X represents $C_1$-$C_6$-alkyl, halogen or $C_1$-$C_6$-alkoxy,
Y represents hydrogen, $C_1$-$C_6$-alkyl, halogen, $C_1$-$C_6$-alkoxy or $C_1$-$C_3$-halogenoalkyl,
Z represents $C_1$-$C_6$-alkyl, halogen or $C_1$-$C_6$-alkoxy,
n represents a number from 0-3,
G represents hydrogen or a metal ion equivalent of an alkali or alkaline earth metal or an ammonium ion.

2. A polycyclic 3-arylpyrrolidine-2,4-dione derivative according to claim 1, in which

is selected from the group consisting of

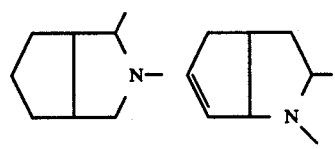

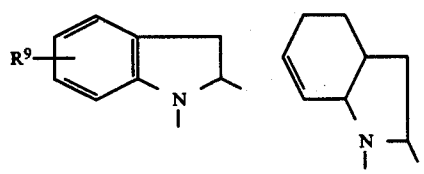

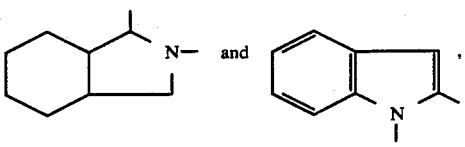

X represents alkyl, halogen or alkoxy,
Y represents hydrogen, alkyl, halogen, alkoxy or halogenoalkyl,
Z represents alkyl, halogen or alkoxy,
n represents a number from 0-3,
G represents hydrogen or a metal ion equivalent of an alkali or alkaline earth metal or an ammonium ion.

3. A polycyclic 3-arylpyrrolidine-2,4-dione derivative of the formula

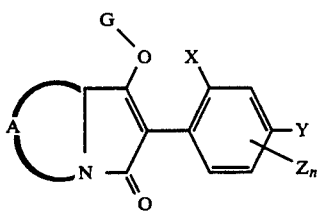

in which
A represents the radical of a bicyclic system wherein the pyrrolidine nitrogen is the sole heteroatom in the resulting tricyclic system,
X represents $C_1$-$C_6$-alkyl, halogen or $C_1$-$C_6$-alkoxy,
Y represents hydrogen, $C_1$-$C_6$-alkyl, halogen, $C_1$-$C_6$-alkoxy or $C_1$-$C_3$-halogenoalkyl,
Z represents $C_1$-$C_6$-alkyl, halogen or $C_1$-$C_6$-alkoxy,
n represents a number from 0-3,
G represents the group

—CO—$R^1$ in which
$R^1$ represents unsubstituted or halogen-substituted: $C_1$-$C_{20}$-alkyl, $C_2$-$C_{20}$-alkenyl, $C_1$-$C_8$-alkoxy-$C_2$-$C_8$-alkyl, $C_1$-$C_8$-alkylthio-$C_2$-$C_8$-alkyl, $C_1$-$C_8$-polyalkoxyl-$C_2$-$C_8$-alkyl or cycloalkyl which has 3-8 ring atoms and which can be interrupted by oxygen and/or sulphur atoms, or represents phenyl which is unsubstituted or substituted by halogen, nitro, $C_1$-$C_6$-alkyl, $C_1$-$C_6$-alkoxy, $C_1$-$C_6$-halogenoalkyl or $C_1$-$C_6$-halogenoalkoxy; or represents phenyl-$C_1$-$C_6$-alkyl, unsubstituted or substituted by halogen, $C_1$-$C_6$-alkyl, $C_1$-$C_6$-alkoxy, $C_1$-$C_6$-halogenoalkoxy, or represents pyridyl, pryimidyl, thiazolyl or pyrazolyl which is unsubstituted or substituted by halogen and/or $C_1$-$C_6$-alkyl, or represents phenoxy-$C_1$-$C_6$-alkyl, unsubstituted or substituted by halogen and/or $C_1$-$C_6$-alkyl, or represents pyridyloxy-$C_1$-$C_4$-alkyl, pyrimidinyloxy-$C_1$-$C_4$-alkyl, thiazolyloxy-$C_1$-$C_4$-alkyl.

4. A polycyclic 3-arylpyrrolidine-2,4-dione derivative of the formula

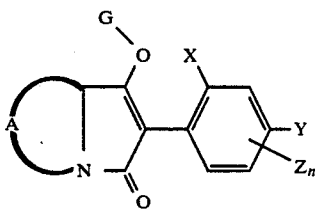

in which
A represents the radical of a bicyclic system wherein the pyrrolidine nitrogen is the sole heteroatom in the resulting tricyclic system,
X represents $C_1$–$C_6$-alkyl, halogen or $C_1$–$C_6$-alkoxy,
Y represents hydrogen, $C_1$–$C_6$-alkyl, halogen, $C_1$–$C_6$-alkoxy or $C_1$–$C_3$-halogenoalkyl,
Z represents $C_1$–$C_6$-alkyl, halogen or $C_1$–$C_6$-alkoxy,
n represents a number from 0–3,
G represents the group

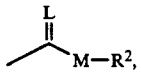  (c)

in which
L and M in each case represents oxygen and/or sulphur,
$R^2$ represents unsubstituted or halogen-substituted $C_1$–$C_{20}$-alkyl, $C_2$–$C_{20}$-alkenyl, $C_1$–$C_8$-alkoxy-$C_2$–$C_8$-alkyl or $C_1$–$C_8$-polyalkoxy-$C_2$–$C_8$-alkyl, or represents phenyl or benzyl, unsubstituted or substituted by halogen, nitro, $C_1$–$C_6$-alkyl, $C_1$–$C_6$-alkoxy or $C_1$–$C_6$-halogenoalkyl, 5. A polycyclic 3-arylpyrrolidine-2,4-dione derivative of the formula

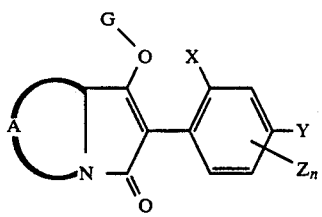

in which
A represents the radical of a bicyclic system wherein the pyrrolidine nitrogen is the sole heteroatom in the resulting tricyclic system,
X represents $C_1$–$C_6$-alkyl, halogen or $C_1$–$C_6$-alkoxy,
Y represents hydrogen, $C_1$–$C_6$-alkyl, halogen, $C_1$–$C_6$-alkoxy or $C_1$–$C_3$-halogenoalkyl,
Z represents $C_1$–$C_6$-alkyl, halogen or $C_1$–$C_6$-alkoxy,
n represents a number from 0–3,
G represents the group

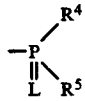  (e)

in which
L represents oxygen and/or sulphur, and
$R^4$ and $R^5$ independently of one another represent $C_1$–$C_8$-alkyl, $C_1$–$C_8$-alkoxy, $C_1$–$C_8$-alkylamino, di-($C_1$–$C_8$)-alkylamino, $C_1$–$C_8$-alkylthio, $C_2$–$C_5$-alkenylthio, $C_2$–$C_5$-alkinylthio or $C_3$–$C_7$-cycloalkylthio, each of which is unsubstituted or substituted by halogen, or represents phenyl, phenoxy or phenylthio, each of which is unsubstituted or substituted by halogen, nitro, cyano, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkyl or $C_1$–$C_4$-halogenoalkyl.

6. A polycyclic 3-arylpyrrolidine-2,4-dione derivative according to claim 1, in which

is selected from the group consisting of

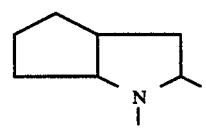 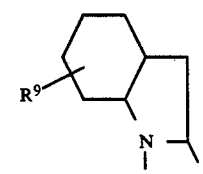

1              2

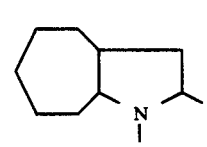 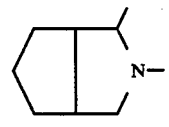

3              4

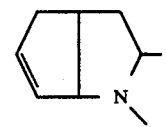 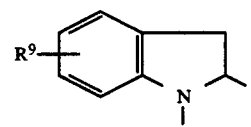

5              6

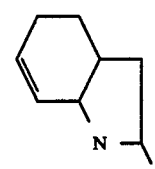 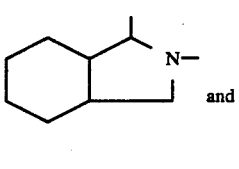 and 7              8

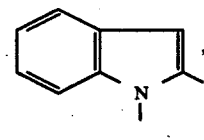

29

X represents methyl, ethyl, propyl, i-propyl, fluorine, chlorine, bromine, methoxy or ethoxy,
Y represents hydrogen, methyl, ethyl, propyl, i-propyl, butyl, i-butyl, tert.-butyl, fluorine, chlorine, bromine, methoxy, ethoxy or trifluoromethyl,
Z represents methyl, ethyl, i-propyl, butyl, i-butyl, tert.-butyl, fluorine, chlorine, bromine, methoxy or ethoxy, n represents a number from 0-3, G represents hydrogen or a metal ion equivalent of an alkali or alkaline earth metal or an ammonium ion.

7. An insecticidal, acaricidal or herbicidal composition comprising an amount effective therefor of a compound according to claim 1 and a diluent.

8. A method of combating insects, acarids or unwanted vegetation which comprises applying to such insects, acarids, unwanted vegetation or to a locus from which it is desired to exclude such insects, acarids or vegetation an amount effective therefor of a compound according to claim 1.

9. A polycyclic 3-arylpyrrolidine-2,4-dione derivative having the following formula:

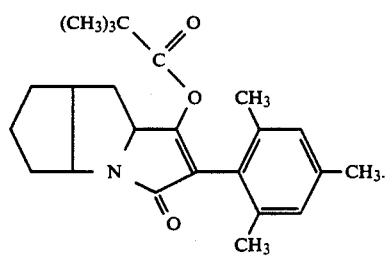

10. A polycyclic 3-arylpyrrolidine-2,4-dione derivative having the following formula:

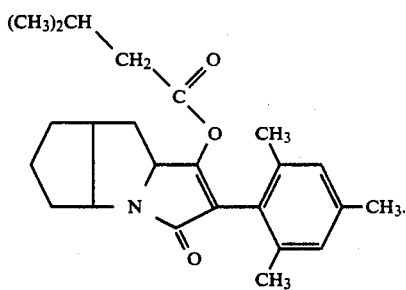

11. A polycyclic 3-arylpyrrolidine-2,4-dione derivative having the following formula:

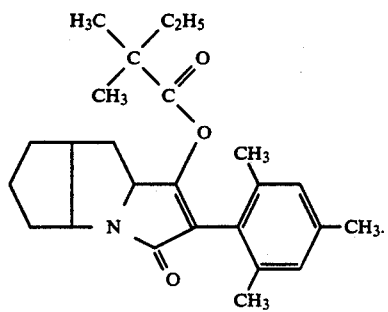

12. A polycyclic 3-arylpyrrolidine-2,4-dione derivative having the following formula:

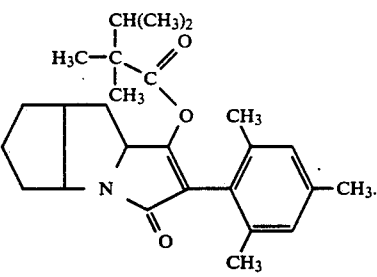

13. A polycyclic 3-arylpyrrolidine-2,4-dione derivative having the following formula:

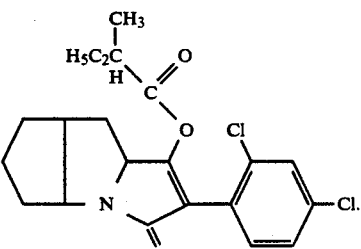

14. A polycyclic 3-arylpyrrolidine-2,4-dione derivative having the following formula:

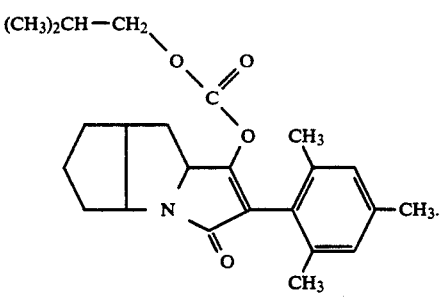

15. A polycyclic 3-arylpyrrolidine-2,4-dione derivative having the following formula:

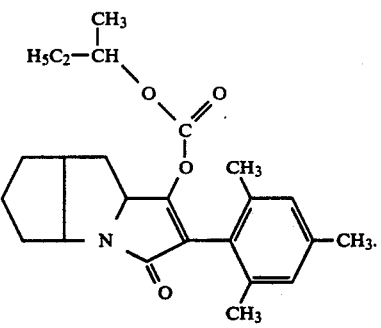

16. A polycyclic 3-arylpyrrolidine-2,4-dione derivative having the following formula:

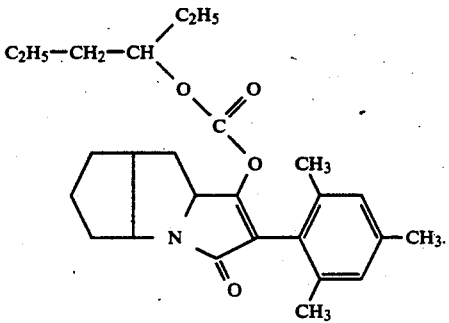

* * * * *